US009917272B2

(12) United States Patent
Voges et al.

(10) Patent No.: US 9,917,272 B2
(45) Date of Patent: Mar. 13, 2018

(54) ELECTRONIC DEVICE

(71) Applicant: Merck Patent GmbH, Darmstadt (DE)

(72) Inventors: Frank Voges, Bad Duerkheim (DE); Jonas Valentin Kroeber, Frankfurt am Main (DE); Christof Pflumm, Darmstadt (DE); Joachim Kaiser, Darmstadt (DE); Arne Buesing, Frankfurt am Main (DE)

(73) Assignee: Merck Patent GmbH (DE)

( * ) Notice: Subject to any disclaimer, the term of this patent is extended or adjusted under 35 U.S.C. 154(b) by 264 days.

(21) Appl. No.: 14/434,277

(22) PCT Filed: Sep. 11, 2013

(86) PCT No.: PCT/EP2013/002727
§ 371 (c)(1),
(2) Date: Apr. 8, 2015

(87) PCT Pub. No.: WO2014/056565
PCT Pub. Date: Apr. 17, 2014

(65) Prior Publication Data
US 2015/0270506 A1  Sep. 24, 2015

(30) Foreign Application Priority Data

Oct. 9, 2012  (EP) ..................... 12006991

(51) Int. Cl.
*H01L 51/50* (2006.01)
*H01L 51/00* (2006.01)
*A61N 5/06* (2006.01)
*H01L 51/52* (2006.01)

(52) U.S. Cl.
CPC ............ *H01L 51/5064* (2013.01); *A61N 5/06* (2013.01); *H01L 51/0059* (2013.01); *H01L 51/5004* (2013.01); *H01L 51/506* (2013.01); *H01L 51/5012* (2013.01); *H01L 51/5072* (2013.01); *H01L 51/5092* (2013.01); *H01L 51/5096* (2013.01); *H01L 51/5206* (2013.01); *H01L 51/5221* (2013.01); *A61N 2005/0653* (2013.01); *H01L 51/006* (2013.01); *H01L 51/0051* (2013.01); *H01L 51/0056* (2013.01); *H01L 51/0058* (2013.01); *H01L 51/0061* (2013.01); *H01L 51/0071* (2013.01); *H01L 51/0072* (2013.01); *H01L 51/0073* (2013.01); *H01L 51/0074* (2013.01); *H01L 51/0094* (2013.01); *H01L 2251/301* (2013.01); *H01L 2251/303* (2013.01); *H01L 2251/308* (2013.01); *H01L 2251/552* (2013.01); *H01L 2251/558* (2013.01)

(58) Field of Classification Search
None
See application file for complete search history.

(56) References Cited

U.S. PATENT DOCUMENTS

| | | | |
|---|---|---|---|
| 6,423,429 B2 * | 7/2002 | Kido | H01L 51/5088 313/502 |
| 7,449,832 B2 | 11/2008 | Rai | |
| 8,691,398 B2 | 4/2014 | Yamada et al. | |
| 8,852,756 B2 | 10/2014 | Vestweber et al. | |
| 8,957,412 B2 | 2/2015 | Yamada et al. | |
| 9,088,002 B2 | 7/2015 | Ikeda et al. | |
| 9,136,495 B2 | 9/2015 | Hamada | |
| 9,472,767 B2 | 10/2016 | Im et al. | |
| 2003/0170491 A1 * | 9/2003 | Liao | H01L 51/5036 428/690 |
| 2005/0255334 A1 * | 11/2005 | Kang | B82Y 10/00 428/690 |
| 2006/0022585 A1 * | 2/2006 | Aziz | H01L 51/506 313/504 |
| 2007/0098891 A1 * | 5/2007 | Tyan | C23C 14/228 427/248.1 |
| 2007/0126348 A1 * | 6/2007 | Iou | H01L 51/004 313/506 |
| 2007/0141396 A1 | 6/2007 | Chun et al. | |
| 2007/0231596 A1 * | 10/2007 | Spindler | H01L 51/5052 428/690 |
| 2008/0193793 A1 * | 8/2008 | Johannes | C07C 255/42 428/690 |
| 2008/0297036 A1 * | 12/2008 | Noh | C09K 11/06 313/504 |
| 2009/0001878 A1 * | 1/2009 | Qiu | H05B 33/22 313/504 |
| 2009/0315022 A1 * | 12/2009 | Morishita | C07D 221/18 257/40 |
| 2010/0045175 A1 * | 2/2010 | Mathai | H01L 27/3209 313/504 |
| 2010/0288362 A1 * | 11/2010 | Hatwar | H01L 51/5044 136/263 |
| 2011/0108818 A1 * | 5/2011 | Kaiser | C09K 11/06 257/40 |
| 2011/0203649 A1 * | 8/2011 | Konemann | C07D 241/38 136/255 |
| 2011/0215308 A1 | 9/2011 | Im et al. | |
| 2011/0233604 A1 * | 9/2011 | Ikeda | H01L 51/5016 257/103 |

(Continued)

FOREIGN PATENT DOCUMENTS

CN     1589073 A      3/2005
CN   101228250 A      7/2008

(Continued)

OTHER PUBLICATIONS

Zhou et al. "Very-low-operating-voltage organic light-emitting diodes using a p-doped amorphous hole injection layer" Applied Physics Letters, 78(4), 2001, 410-412.*

(Continued)

*Primary Examiner* — Robert S Loewe
(74) *Attorney, Agent, or Firm* — Drinker Biddle & Reath LLP

(57) ABSTRACT

The present application relates to an electronic device comprising a hole-transport layer A, a doped hole-transport layer B and a hole-transport layer C, where hole-transport layers A, B and C are arranged between the anode and the emitting layer, and where hole-transport layer B is arranged on the cathode side of hole-transport layer A and hole-transport layer C is arranged on the cathode side of hole-transport layer B.

24 Claims, No Drawings

(56) References Cited

U.S. PATENT DOCUMENTS

| | | | |
|---|---|---|---|
| 2011/0256422 A1* | 10/2011 | Reichelt | B82Y 10/00 428/704 |
| 2011/0297977 A1 | 12/2011 | Kajimoto | |
| 2012/0012820 A1* | 1/2012 | Endo | H01L 51/5278 257/40 |
| 2012/0074392 A1* | 3/2012 | Huang | H01L 27/3209 257/40 |
| 2012/0076836 A1 | 3/2012 | Hori et al. | |
| 2013/0284977 A1* | 10/2013 | Kunz | C07F 1/00 252/301.16 |
| 2014/0316134 A1 | 10/2014 | Stoessel et al. | |
| 2015/0031896 A1 | 1/2015 | Vestweber et al. | |
| 2016/0099421 A1* | 4/2016 | Kim | H01L 51/0067 257/40 |
| 2016/0343776 A1* | 11/2016 | Heo | H01L 27/322 |

FOREIGN PATENT DOCUMENTS

| | | |
|---|---|---|
| CN | 102201432 A | 9/2011 |
| CN | 102270655 A | 12/2011 |
| EP | 1801882 A2 | 6/2007 |
| EP | 2365555 A2 | 9/2011 |
| JP | 2008019238 A | 1/2008 |
| JP | 2008177455 A | 7/2008 |
| JP | 2009071189 A | 4/2009 |
| JP | 2010123716 A | 6/2010 |
| JP | 2011187959 A | 9/2011 |
| JP | 2012182443 A | 9/2012 |
| KR | 20080090350 A | 10/2008 |
| KR | 20110101418 A | 9/2011 |
| KR | 20110125861 A | 11/2011 |
| TW | I299636 B | 8/2008 |
| WO | WO-2004091262 A1 | 10/2004 |
| WO | WO-2006/122630 A1 | 11/2006 |
| WO | WO-2012073269 A1 | 6/2012 |
| WO | WO-2012076836 A1 | 6/2012 |
| WO | WO-2013/083216 A1 | 6/2013 |
| WO | WO-2013/135352 A1 | 9/2013 |

OTHER PUBLICATIONS

Chinese Office Action for application No. 201380052539.5, dated May 4, 2016.

International Search Report for PCT/EP2013/002727 dated Oct. 16, 2013.

Japanese Office Action for Japanese Application No. 2015-536003, dated Jul. 4, 2017.

English Translation of Korean Office Action for Korean Application No. 10-2015-7012027, dated Jul. 26, 2017.

* cited by examiner

ELECTRONIC DEVICE

CROSS-REFERENCE TO RELATED APPLICATIONS

This application is a national stage application (under 35 U.S.C. § 371) of PCT/EP2013/002727, filed Sep. 11, 2013, which claims benefit of European Application No. 12006991.9, filed Oct. 9, 2012, both of which are incorporated herein by reference in their entirety.

The present application relates to an electronic device comprising a hole-transport layer A, a doped hole-transport layer B and a hole-transport layer C, where hole-transport layers A, B and C are arranged between the anode and the emitting layer, and where hole-transport layer B is arranged on the cathode side of hole-transport layer A and hole-transport layer C is arranged on the cathode side of hole-transport layer B.

Electronic devices in the sense of this application are taken to mean, in particular, so-called organic electronic devices, which comprise organic semiconductor materials as functional materials. These are again taken to mean, in particular, organic electroluminescent devices (OLEDs) and other electronic devices which are mentioned below.

The structure of OLEDs in which organic semiconductors are employed as functional materials is described, for example, in U.S. Pat. No. 4,539,507, U.S. Pat. No. 5,151,629, EP 0676461 and WO 98/27136.

In the case of the electronic devices concerned, in particular OLEDs, there is considerable interest in improving the performance data, in particular lifetime, efficiency and operating voltage.

The efficiency and lifetime of electronic devices, such as OLEDs, are determined, inter alia, by the charge-carrier balance of electrons and holes in the device. This balance becomes established through the charge-carrier distribution and the associated field distribution in the device.

For good performance data, good mobilities of the charge carriers in the hole-transport layers and good hole-injection properties are particularly crucial. Furthermore, it is of crucial importance that the difference of the HOMOs of the materials of the various hole-transport layers is not excessive.

The prior art discloses the use of a p-doped hole-transport layer, followed by an undoped electron-blocking layer, between the anode and the emitting layer (WO 20021041414). In this case, the p-doped hole-transport layer is not followed by a further hole-transport layer, but instead directly by the emitting layer.

The prior art furthermore discloses the use of two or more hole-transport layers between the anode and the emitting layer (WO 2010/094378).

On the basis of this prior art, the technical object is to provide electronic devices, in particular OLEDs, which have improved performance data, in particular in respect of lifetime and efficiency.

Surprisingly, it has now been found that the use of a p-doped hole-transport layer between a first hole-transport layer and a further hole-transport layer, regarded from the anode, causes an improvement in the above-mentioned points and thus achieves the technical object.

The present application thus relates to an electronic device comprising anode, cathode and at least one emitting layer arranged between the anode and the cathode, and at least one hole-transport layer A, comprising at least one hole-transport material at least one p-doped hole-transport layer B, comprising at least one p-dopant and at least one hole-transport material matrix at least one hole-transport layer C, comprising at least one hole-transport material, where hole-transport layers A, B and C are arranged between the anode and the emitting layer, and where hole-transport layer B is arranged on the cathode side of hole-transport layer A, and hole-transport layer C is arranged on the cathode side of hole-transport layer B.

The electronic device according to the invention has the advantage that it has higher efficiency, preferably combined with a longer lifetime. Furthermore, it can be operated at comparatively low voltage.

The device according to the invention furthermore has the advantage that materials having a low HOMO can thus be used in a hole-transport layer, in particular in combination with materials having a higher HOMO in another hole-transport layer.

The fact that, in accordance with the invention, only hole-transport layer B has to be p-doped means that the amount of p-dopant required and thus the costs are lower compared with a structure in which all hole-transport layers are p-doped. This represents an advantage over devices in accordance with the prior art in which all hole-transport layers are p-doped.

A hole-transport layer for the purposes of the present application is taken to mean an organic layer which has hole-transporting properties. In particular, it is taken to mean an organic layer which is located between the anode and the emitting layer and has hole-transporting properties. A hole-transport material is correspondingly taken to mean a material having hole-transporting properties.

A p-dopant is taken to mean a compound which is able to at least partially oxidise the other compound (the matrix) present in the layer and in this way increases the conductivity of the layer. p-Dopants in accordance with the present application are typically organic electron-acceptor compounds.

A matrix here denotes the compound or compounds which represent the predominant component (% by weight) in a layer comprising a dopant. Correspondingly, the dopant represents the component present in lower amount in the corresponding layer. A corresponding situation applies to the specific terms hole-transport material matrix and p-dopant.

The electronic device according to the invention is preferably selected from organic light-emitting transistors (OLETs), organic light-emitting electrochemical cells (OLECs), organic laser diodes (O-lasers) and organic electroluminescent devices (OLEDs).

Particular preference is given to organic electroluminescent devices (OLEDs).

The anode of the electronic device preferably consists of a material having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/NiO$_x$, Al/PtO$_x$) may also be preferred. For some applications, at least one of the electrodes must be transparent or partially transparent in order to facilitate either the irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive doped polymers.

According to a preferred embodiment of the invention, the electronic device is characterised in that the anode comprises tungsten oxide, molybdenum oxide and/or vanadium oxide, and/or in that a p-doped hole-transport layer A', comprising at least one p-dopant and a hole-transport material matrix, is arranged between the anode and hole-transport layer A.

The above-mentioned anode comprising tungsten oxide, molybdenum oxide and/or vanadium oxide is preferably built up in such a way that it consists of indium tin oxide (ITO) which has been coated with tungsten oxide, molybdenum oxide and/or vanadium oxide.

Hole-transport layer A' preferably comprises a p-dopant selected from organic electron-acceptor compounds.

Particularly preferred embodiments of p-dopants are described below in connection with p-dopants of hole-transport layer B.

The p-dopant in hole-transport layer A' is preferably present in a concentration of 0.1 to 20% by vol., preferably 0.5 to 12% by vol., particularly preferably 1 to 8% by vol. and very particularly preferably 2 to 6% by vol.

The hole-transport material matrix of hole-transport layer A' can be any desired organic material having hole-transporting properties.

The hole-transport material matrix for hole-transport layer A' is preferably indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic ring systems (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenemonotriarylamines (for example in accordance with WO 2012/034627 or the as yet unpublished EP 12000929.5), spirobifluorenetetrakistriarylamines, for example spiro-TAD or spiro-TTB, fluorenamines (for example in accordance with the as yet unpublished applications EP 12005369.9, EP 12005370.7 and EP 12005371.5), spirodibenzopyranamines (for example in accordance with WO 2013/083216) and dihydroacridine derivatives (for example in accordance with WO 2012/150001).

The hole-transport material matrix is preferably selected from triarylamine compounds, preferably monotriarylamine compounds, particularly preferably from monotriarylamine compounds from the structure classes mentioned above.

Alternatively, it may also be preferred for the hole-transport material matrix to be selected from bistriarylamine compounds or polytriarylamine compounds, for example tetrakistriarylamine compounds.

A triarylamine compound is taken to mean a compound which contains one or more triarylamine groups. A monotriarylamine compound is taken to mean a compound which contains a single triarylamine group. A triarylamine group is a group in which three aryl or heteroaryl groups are bonded to a common nitrogen atom. A monotriarylamine compound preferably contains no further arylamino group. A monotriarylamine compound particularly preferably contains no further amino group. Analogously, bistriarylamine compounds and tetrakistriarylamine compounds area defined as compounds which contain two or four triarylamine groups respectively.

Hole-transport layer A is preferably in direct contact with the anode or hole-transport layer N.

Hole-transport layer A preferably has a thickness of 100 to 300 nm, particularly preferably 130 to 230 nm.

Preferred hole-transport materials which are present in hole-transport layer A are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic ring systems (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenemonotriarylamines (for example in accordance with WO 2012/034627 or the as yet unpublished EP 12000929.5), spirobifluorenetetrakistriarylamines, for example spiro-TAD or spiro-TTB, fluorenamines (for example in accordance with the as yet unpublished applications EP 12005369.9, EP 12005370.7 and EP 12005371.5), spirodibenzopyranamines (for example in accordance with WO 2013/083216) and dihydroacridine derivatives (for example in accordance with WO 2012/150001).

The hole-transport material is preferably selected from triarylamine compounds, preferably monotriarylamine compounds, particularly preferably from monotriarylamine compounds from the structure classes mentioned above.

Alternatively, it may also be preferred for the hole-transport material to be selected from bistriarylamine compounds or polytriarylamine compounds, for example tetrakistriarylamine compounds.

According to a preferred embodiment, hole-transport layer A comprises the same compound as hole-transport material as hole-transport layer A' does as hole-transport material matrix.

Hole-transport layer A furthermore preferably comprises no p-dopant. It particularly preferably comprises a single compound, i.e. is not a mixed layer.

Hole-transport layer B is p-doped in accordance with the invention.

According to a preferred embodiment, hole-transport layer B is in direct contact with hole-transport layer A.

Preferred hole-transport material matrices of hole-transport layer B belong to the same structure classes as described above for hole-transport layer A. In particular, these are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic ring systems (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or the as yet unpublished EP 12000929.5), spirobifluorenetetrakistriarylamines, for example spiro-TAD or spiro-TTB, fluorenamines (for example in accordance with the as yet unpublished applications EP 12005369.9, EP 12005370.7 and EP 12005371.5), spirodibenzopyranamines (for example in accordance with WO 2013/083216) and dihydroacridine derivatives (for example in accordance with WO 2012/150001).

The hole-transport material of layer B is preferably selected from triarylamine compounds, preferably monotriarylamine compounds, particularly preferably from monotriarylamine compounds from the structure classes mentioned above.

Particularly preferred embodiments of p-dopants, in particular for the p-doped hole-transport layers A' and B, are the compounds disclosed in WO 2011/073149, EP 1968131, EP 2276085, EP 2213662, EP 1722602, EP 2045848, DE 102007031220, U.S. Pat. No. 8,044,390, U.S. Pat. No. 8,057,712, WO 2009/003455, WO 2010/094378, WO 2011/120709, US 2010/0096600 and WO 2012/095143.

Particularly preferred p-dopants are quinodimethane compounds, azaindenofluorenediones, azaphenalenes, azatriphenylenes, $I_2$, metal halides, preferably transition-metal halides, metal oxides, preferably metal oxides containing at least one transition metal or a metal from main group 3, and transition-metal complexes, preferably complexes of Cu, Co, Ni, Pd and Pt with ligands containing at least one oxygen atom as bonding site. Preference is furthermore given to transition-metal oxides as dopants, preferably oxides of rhenium, molybdenum and tungsten, particularly preferably $Re_2O_7$, $MoO_3$, $WO_3$ and $ReO_3$.

The p-dopants are preferably substantially uniformly distributed in the p-doped layers. This can be achieved, for example, by co-evaporation of the p-dopant and the hole-transport material matrix.

The p-dopants are particularly preferably the following compounds:

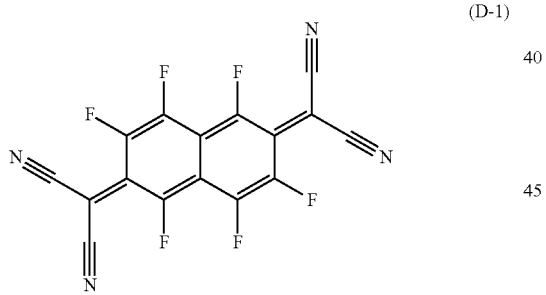
(D-1)

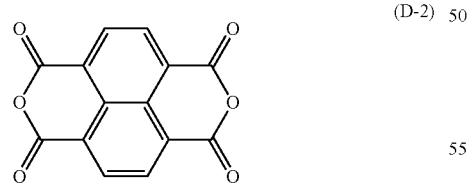
(D-2)

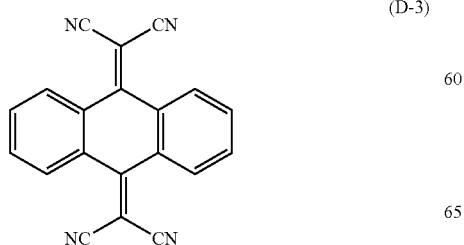
(D-3)

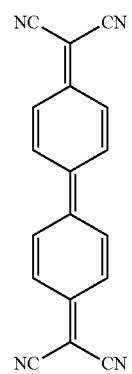
(D-4)

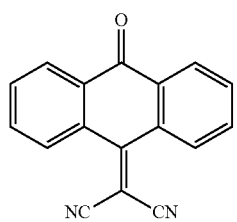
(D-5)

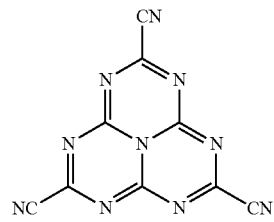
(D-6)

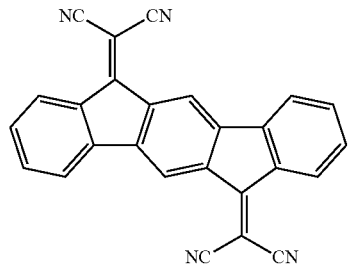
(D-7)

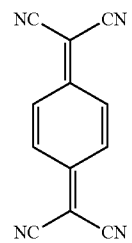
(D-8)

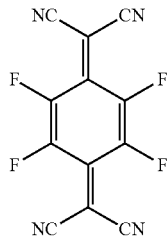
(D-9)

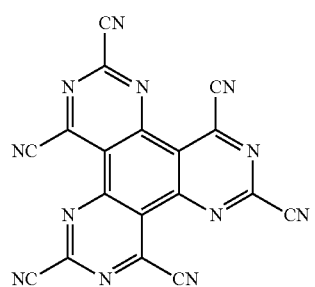

(D-10)

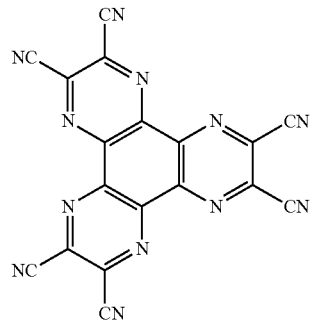

(D-11)

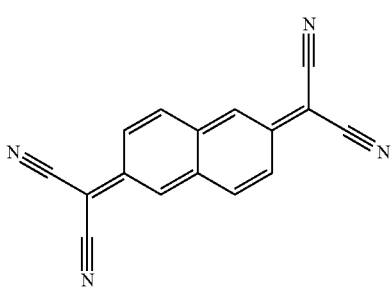

(D-12)

The p-dopant is preferably present in hole-transport layer B in a concentration of 0.1 to 20% by vol., preferably 0.5 to 12% by vol., particularly preferably 1 to 8% by vol. and very particularly preferably 2 to 6% by vol.

Hole-transport layer B preferably has a thickness of 5 to 50 nm, particularly preferably 10 to 40 nm.

Hole-transport layer C preferably comprises no p-dopant. It particularly preferably comprises a single compound, i.e. is not a mixed layer.

According to a preferred embodiment, hole-transport layer C is in direct contact with hole-transport layer B. It is furthermore preferably in direct contact with the emitting layer on the anode side.

Preferred hole-transport materials of hole-transport layer C belong to the same structure classes as described above for hole-transport layer A. In particular, these are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic ring systems (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for (for example in accordance with WO 2012/034627 or the as yet unpublished EP 12000929.5), spirobifluorenetetrakistriarylamines, for example spiro-TAD or spiro-TTB, fluorenamines (for example in accordance with the as yet unpublished applications EP 12005369.9, EP 12005370.7 and EP 12005371.5), spirodibenzopyranamines (for example in accordance with WO 2013/083216) and dihydroacridine derivatives (for example in accordance with WO 2012/150001).

The hole-transport material of layer C is preferably selected from triarylamine compounds, preferably monotriarylamine compounds, particularly preferably from monotriarylamine compounds from the structure classes mentioned above.

Hole-transport layer C preferably has a thickness of 5 to 50 nm, particularly preferably 10 to 40 nm.

According to a preferred embodiment, the hole-transport materials of hole-transport layers A and C are different.

It is preferred for the HOMO of the hole-transport material of hole-transport layer C to be between −4.9 and −5.6 eV, preferably between −5.0 and −5.5 eV, and particularly preferably between −5.1 and −5.4 eV.

It is preferred for the HOMO of the hole-transport material of hole-transport layer A to be higher than the HOMO of the hole-transport material of hole-transport layer C by an amount of at least 0.2 eV, preferably at least 0.3 eV, particularly preferably at least 0.4 eV.

The value for the HOMO of the hole-transport material of hole-transport layer A is preferably between −4.7 and −5.4 eV, preferably between −4.8 and −5.3 eV, and particularly preferably between −4.9 eV and −5.2 eV.

The HOMO (highest occupied molecular orbital) is determined here by quantum-chemical calculations and calibrated with reference to cyclic voltammetry measurements, as explained in greater detail in the working examples.

According to a further preferred embodiment, hole-transport layer B comprises the same compound as hole-transport material matrix as hole-transport layer C does as hole-transport material.

In a further preferred embodiment, hole-transport layer A comprises a bistriarylamine compound or polytriarylamine compound, for example a tetrakistriarylamine compound, and hole-transport layer C comprises a monotriarylamine compound. Hole-transport layer A particularly preferably comprises a bistriarylamine compound or polytriarylamine compound, for example a tetrakistriarylamine compound, and hole-transport layers B and C comprise a monotriarylamine compound.

It is preferred in accordance with the invention for hole-transport layers A, B and C and, if present, hole-transport layer A' to be directly adjacent to one another. In addition, it is preferred for the emitting layer or one of the emitting layers to be directly adjacent to hole-transport layer C.

It is preferred for hole-transport layers A, B, C and, if present, A' each to comprise one or more identical or different triarylamine compounds.

They preferably each comprise one or more identical or different monotriarylamine compounds.

It is furthermore preferred for at least one of hole-transport layers A, B, C and A' to comprise at least one compound of one of the formulae

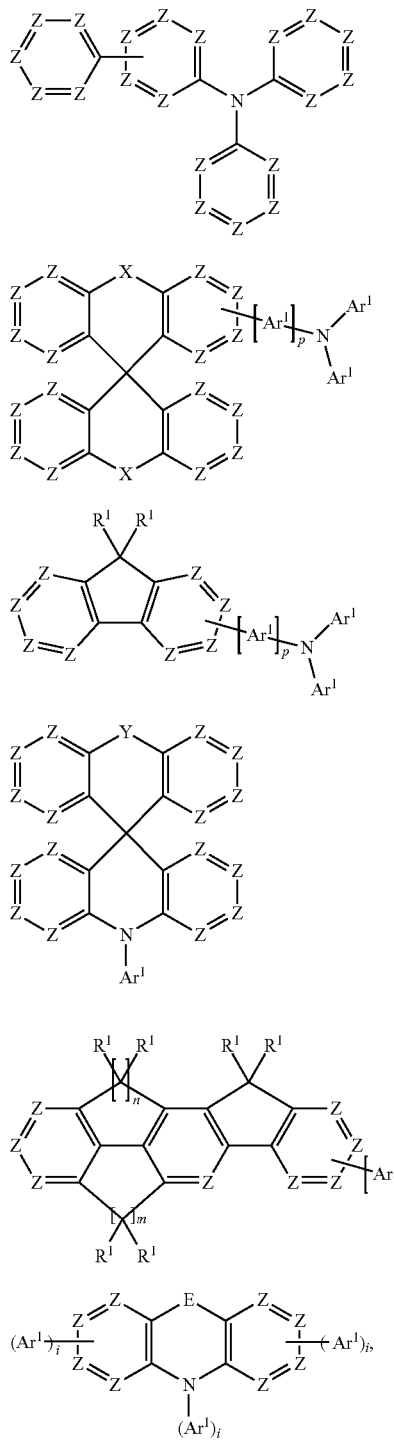

formula (I)
formula (II)
formula (III)
formula (IV)
formula (V)
formula (VI)

where:

Z is on each occurrence, identically or differently, N or CR$^1$, where Z is equal to C if a substituent is bonded;

X, Y are on each occurrence, identically or differently, a single bond, O, S, Se, BR$^1$, C(R$^1$)$_2$, Si(R$^1$)$_2$, NR$^1$, PR$^1$, C(R$^1$)$_2$—C(R$^1$)$_2$ or CR$^1$=CR$^1$;

E is O, S, Se, BR$^1$, C(R$^1$)$_2$, Si(R$^1$)$_2$, NR$^1$, PR$^1$, C(R$^1$)$_2$—C(R$^1$)$_2$ or CR$^1$=CR$^1$;

Ar$^1$ is on each occurrence, identically or differently, an aromatic or heteroaromatic ring system having 5 to 60 aromatic ring atoms, which may be substituted by one or more radicals R$^1$; and R$^1$ is on each occurrence, identically or differently, H, D, F, Cl, Br, I, CHO, C(=O)R$^2$, P(=O)(R$^2$)$_2$, S(=O)R$^2$, S(=O)$_2$R$^2$, CR$^2$=CR$^2$R$^2$, CN, NO$_2$, Si(R$^2$)$_3$, OSO$_2$R$^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R$^2$, where one or more non-adjacent CH$_2$ groups may be replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^2$, or a combination of these systems; two or more adjacent substituents R$^1$ here may also form a mono- or polycyclic, aliphatic or aromatic ring system with one another;

R$^2$ is on each occurrence, identically or differently, H, D, CN or an aliphatic, aromatic and/or heteroaromatic hydrocarbon radical having 1 to 20 C atoms, in which, in addition, H atoms may be replaced by D or F; two or more adjacent substituents R$^2$ here may also form a mono- or polycyclic, aliphatic or aromatic ring system with one another;

i is on each occurrence, identically or differently, 0 or 1, where the sum of all i is at least equal to 1;

p is equal to 0 or 1;

m, n are, identically or differently, 0 or 1, where the sum of m and n is equal to 1 or 2.

At least two of hole-transport layers A, B, C and A' preferably comprise at least one compound of one of the formulae (I) to (VI), particularly preferably at least three of hole-transport layers A, B, C and A', and very particularly preferably all of hole-transport layers A, B, C and A'.

In hole-transport layer A, compounds of the formulae (I), (II), (III) and (V) are preferably employed.

For the above-mentioned formulae (I) to (VI), it is preferred for not more than three groups Z in a ring to be equal to N. It is generally preferred for Z to be equal to CR$^1$.

The group X is preferably selected on each occurrence, identically or differently, from a single bond, C(R$^1$)$_2$, O and S and is particularly preferably a single bond.

The group Y is preferably selected from O and C(R$^1$)$_2$ and is particularly preferably O.

The group E is preferably selected from C(R$^1$)$_2$, O and S and is particularly preferably C(R$^1$)$_2$.

The group Ar$^1$ is selected on each occurrence, identically or differently, from aromatic or heteroaromatic ring systems having 6 to 30 aromatic ring atoms, which may be substituted by one or more radicals R$^1$. Ar$^1$ is particularly preferably selected from aryl or heteroaryl groups having 6 to 18 aromatic ring atoms, which may be substituted by one or more radicals R$^1$.

R$^1$ is selected on each occurrence, identically or differently, from H, D, F, Cl, Br, I, C(=O)R$^2$, CN, Si(R$^2$)$_3$, N(R$^2$)$_2$, NO$_2$, P(=O)(R$^2$)$_2$, S(=O)R$^2$, S(=O)$_2$R$^2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals R$^2$ and where one or more CH$_2$ groups in the above-mentioned groups may be replaced by —$R^2C=CR^2$—, $Si(R^2)_2$, C=O, C=S, C=$NR^2$, —C(=O)O—, —C(=O)$NR^2$—, $NR^2$, P(=O)($R^2$), —O—, —S—, SO or $SO_2$ and where one or more H atoms in the above-mentioned groups may be replaced by D, F, Cl, Br, I, CN or $NO_2$, or an aromatic or heteroaromatic ring system having 5 to 30 aromatic ring atoms, which may in each case be substituted by one or more radicals $R^2$, where two or more radicals $R^1$ may be linked to one another and may form a ring.

The following definitions apply in general:

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals are able to form a ring with one another is intended for the purposes of the present application to be taken to mean, inter alia, that the two radicals are linked to one another by a chemical bond. Furthermore, however, the above-mentioned formulation is also intended to be taken to mean that, in the case where one of the two radicals is hydrogen, the second radical is bonded to the position to which the hydrogen atom was bonded, with formation of a ring.

Examples of preferred hole-transport materials for use in the electronic device in accordance with the present invention, in particular in layers A', A, B and C, are shown below.

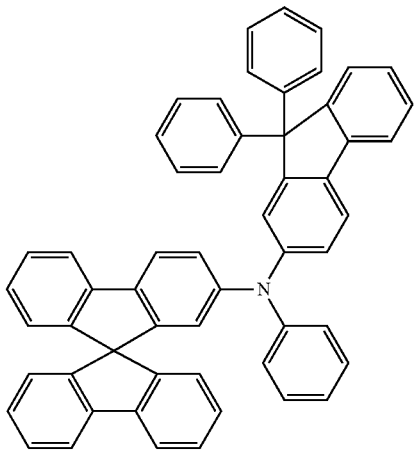
(1)

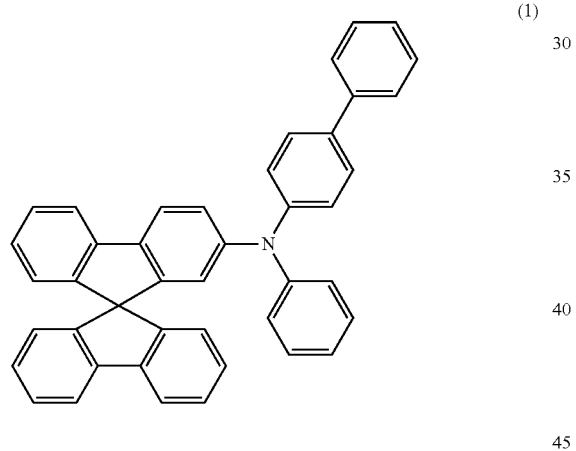
(2)

-continued

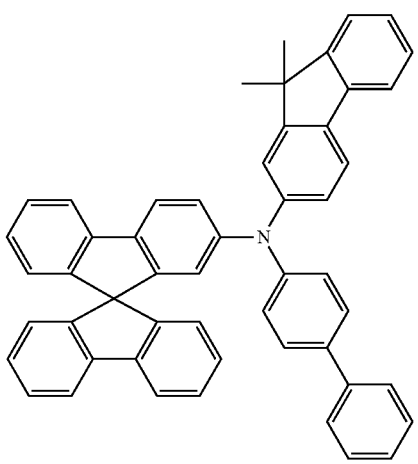
(3)

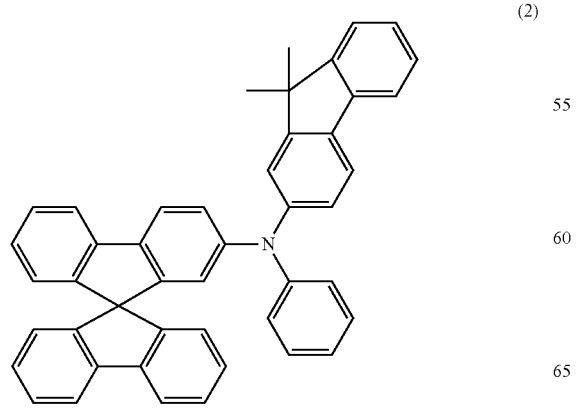
(4)

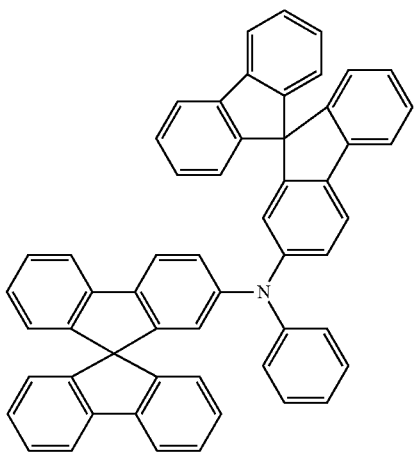
(5)

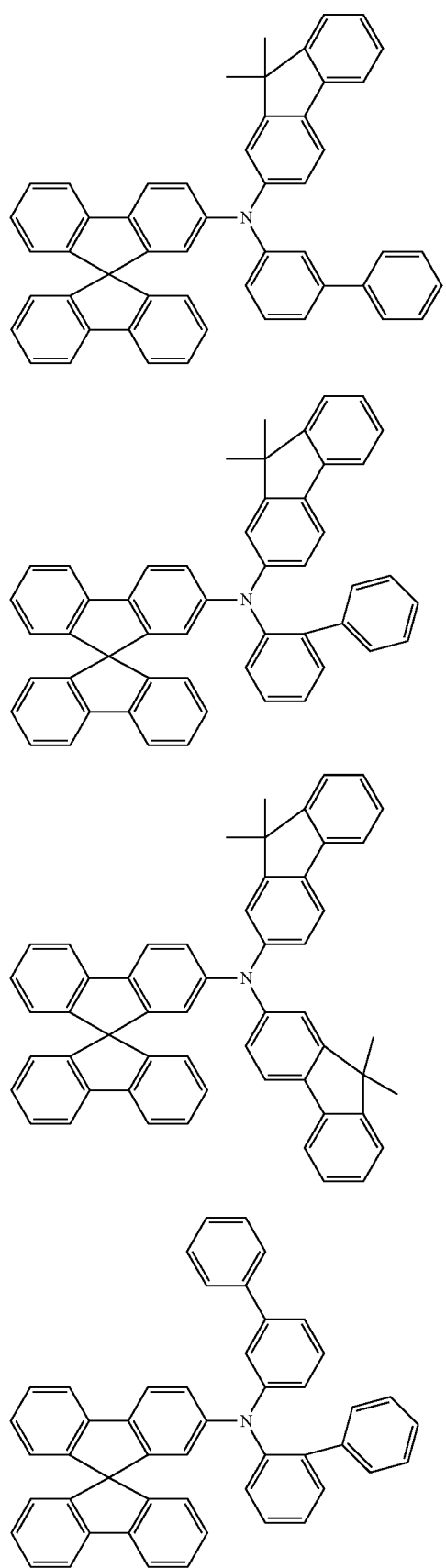
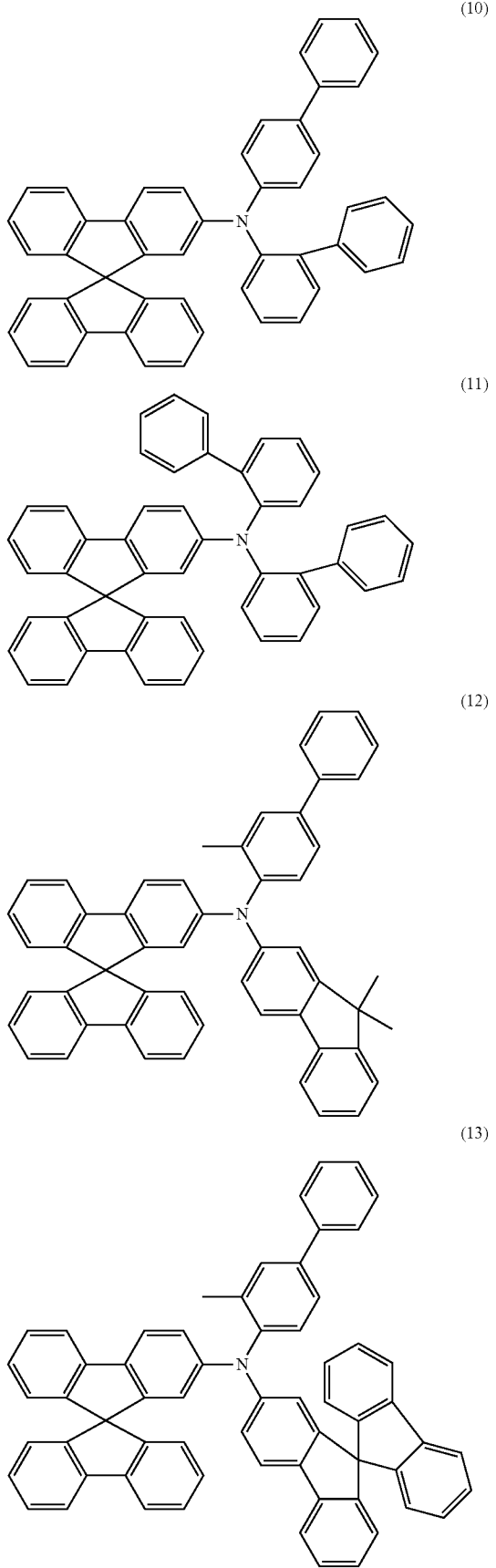

(14)
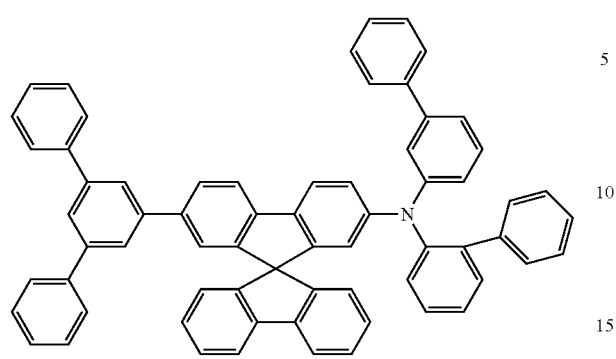
(15)
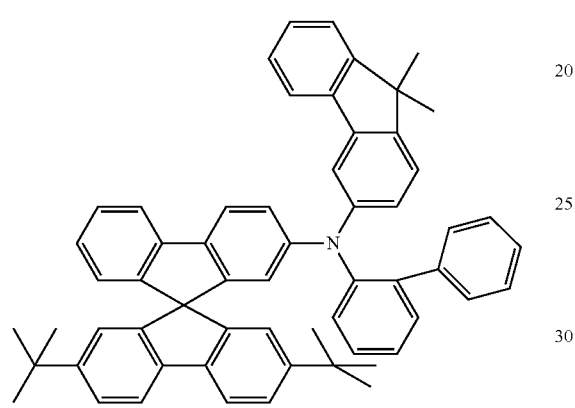
(16)
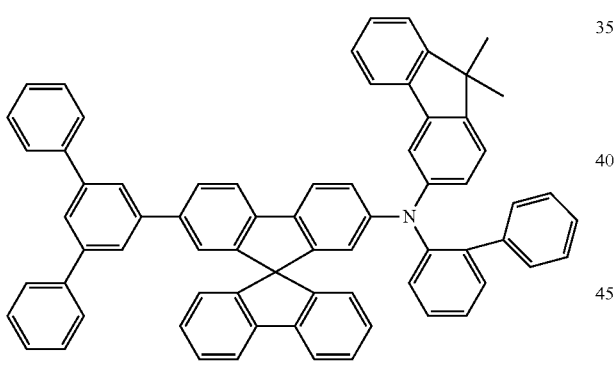
(17)
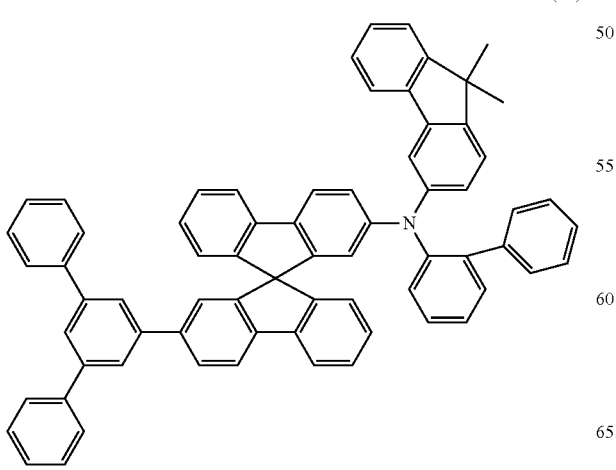
(18)
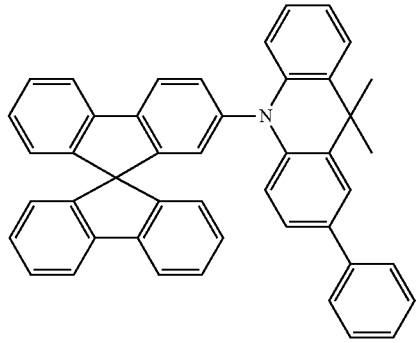
(19)
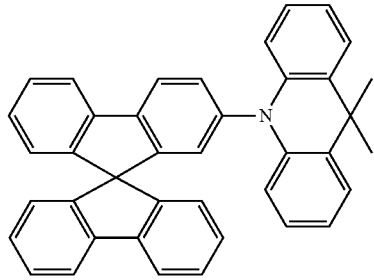
(20)
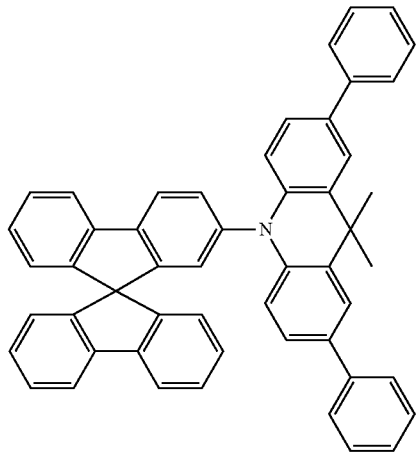
(21)
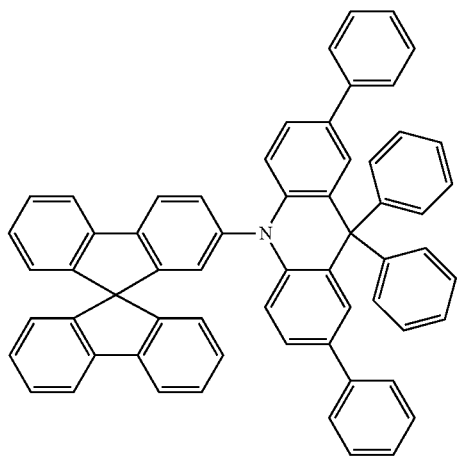

(22)
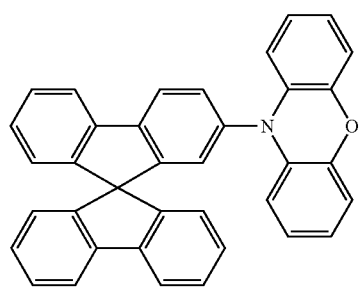
(23)
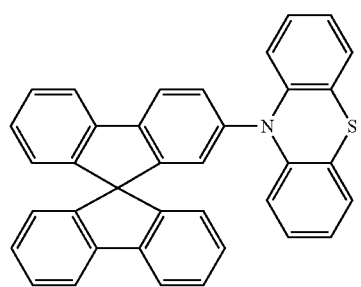
(24)
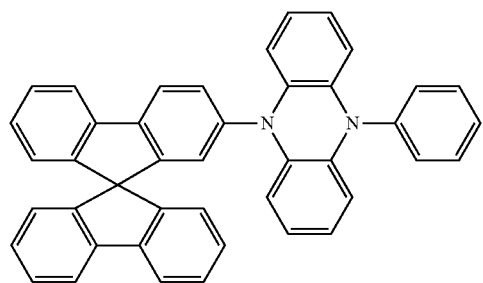
(25)
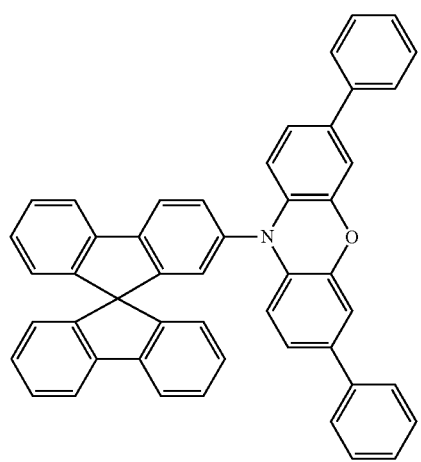
(26)
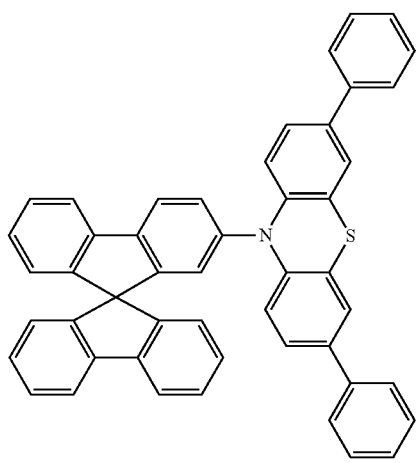
(27)
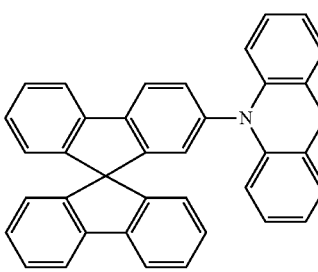
(28)
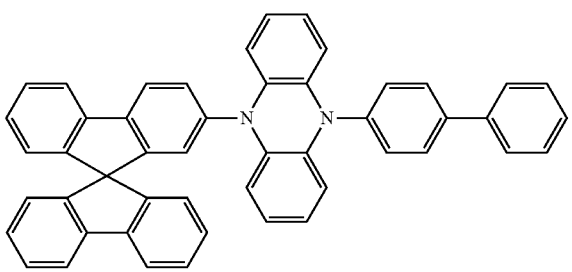

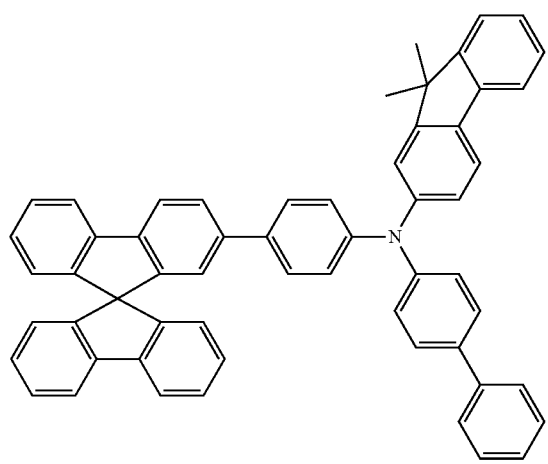
(29)
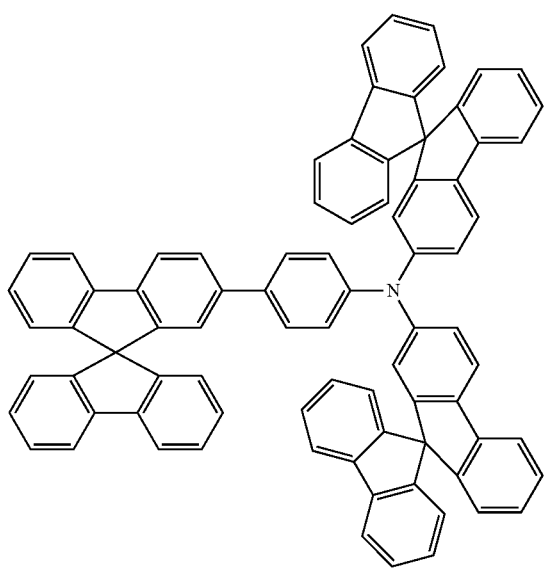
(32)
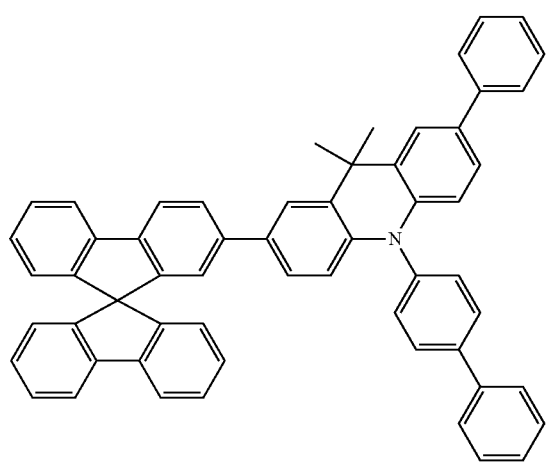
(30)
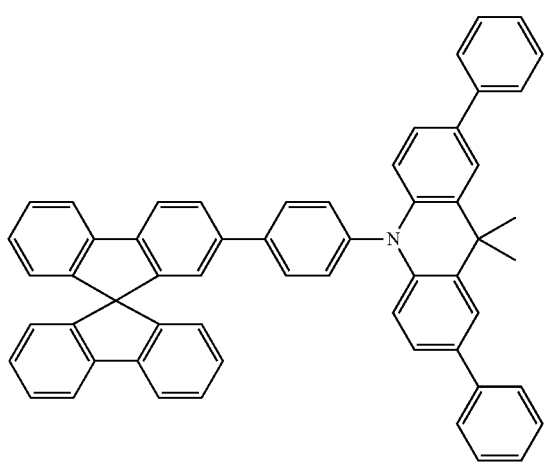
(33)
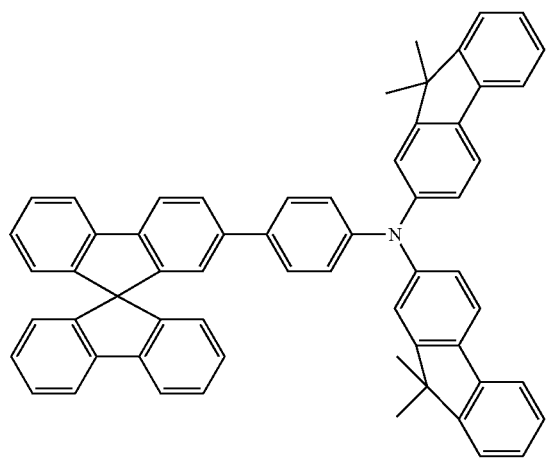
(31)
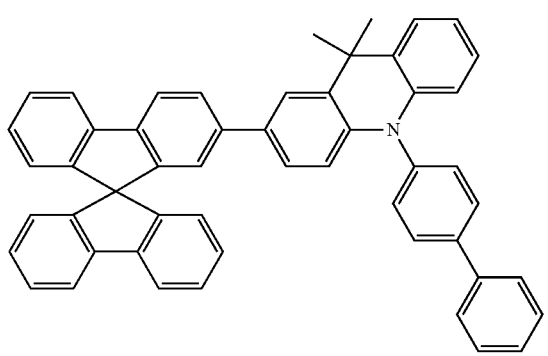
(34)

(35)
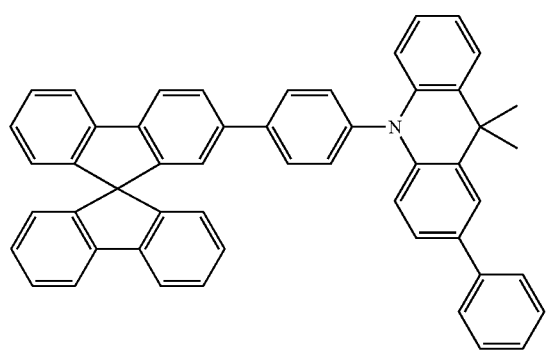
(36)
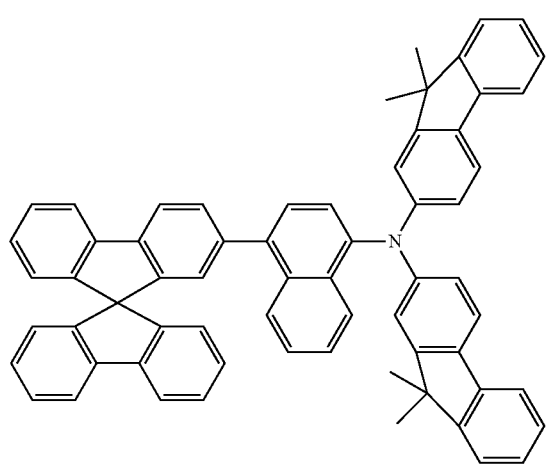
(37)
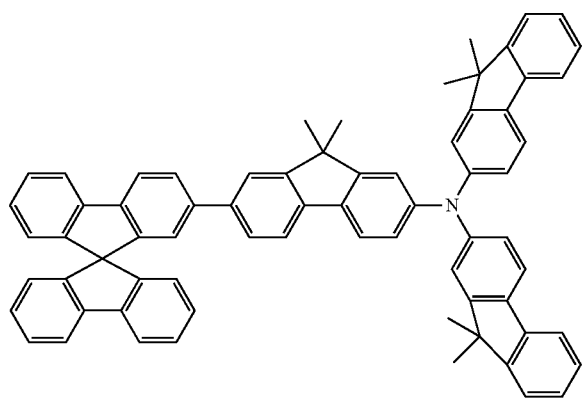
(38)
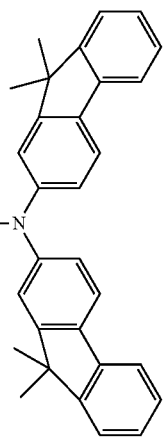
(39)
(40)
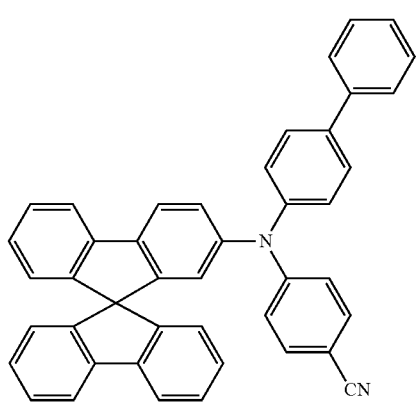

(41)
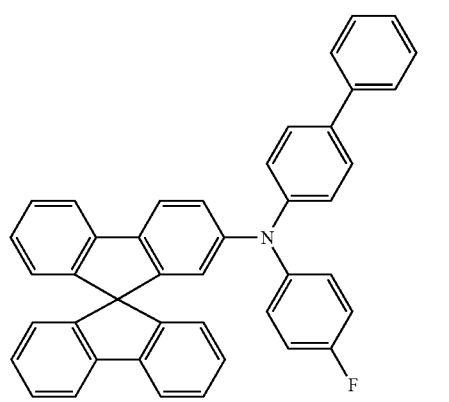
(42)
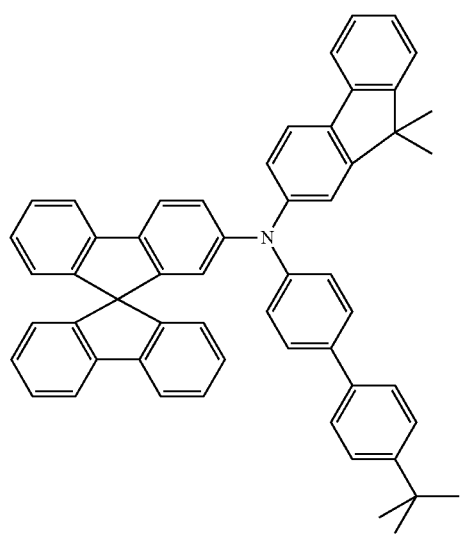
(43)
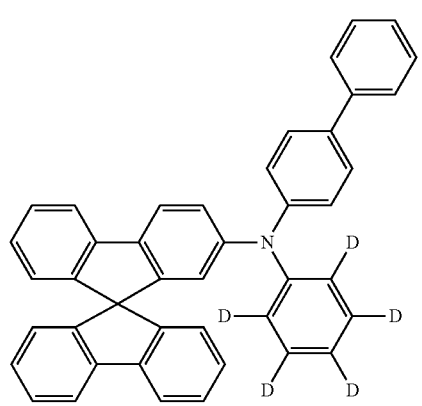
(44)
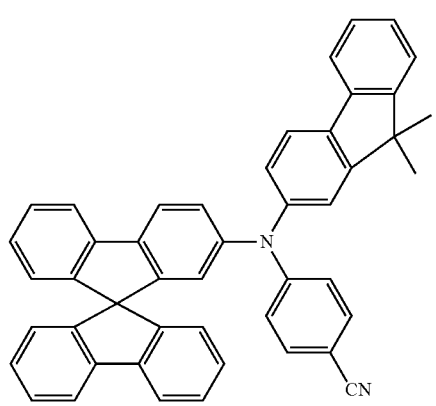
(45)
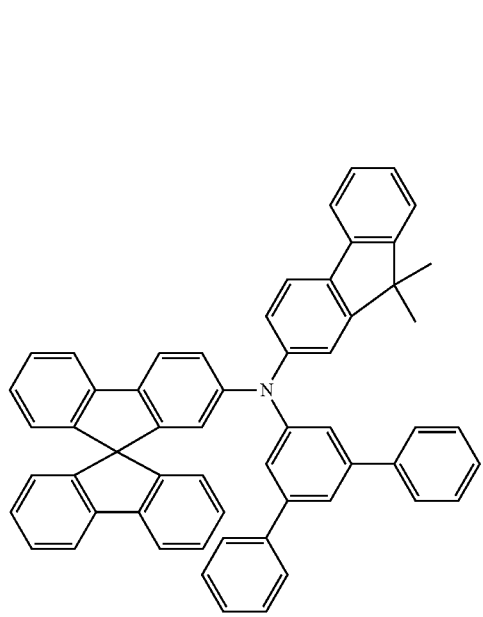
(46)
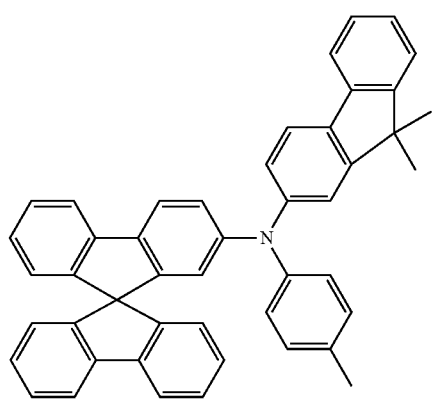

(47)
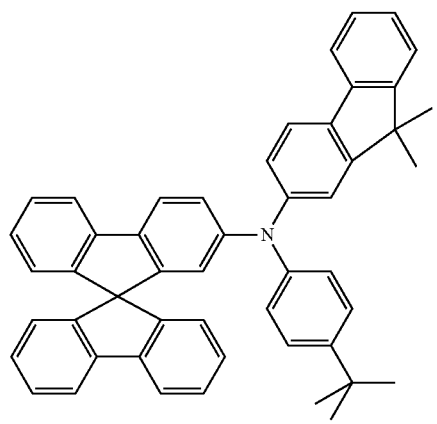
(50)
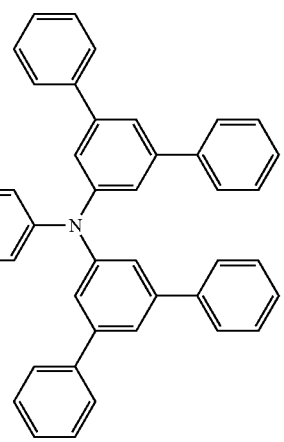
(48)
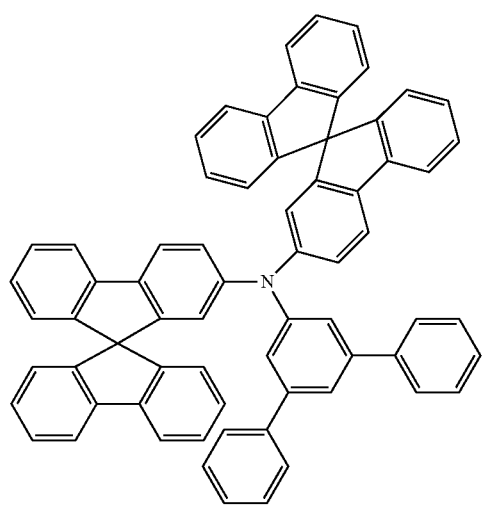
(51)
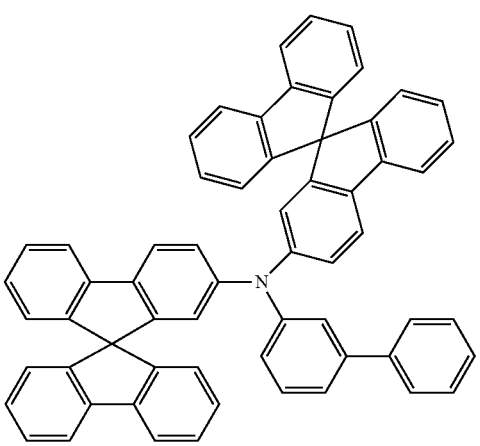
(49)
(52)
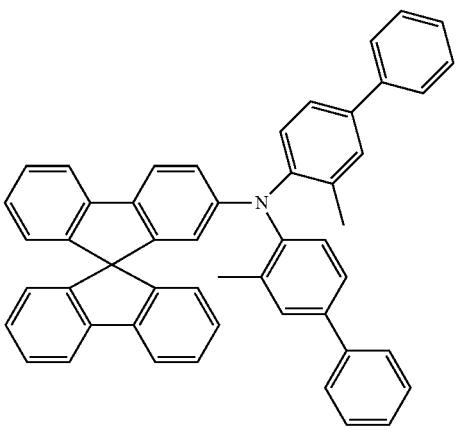

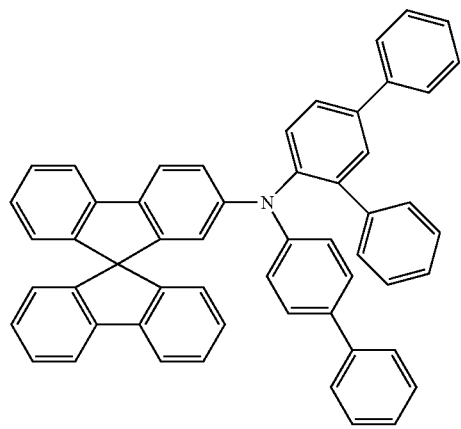
(53)
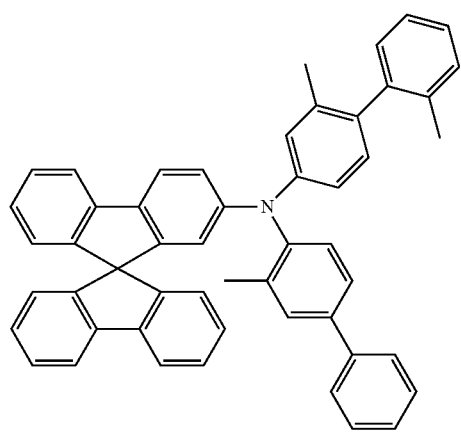
(54)
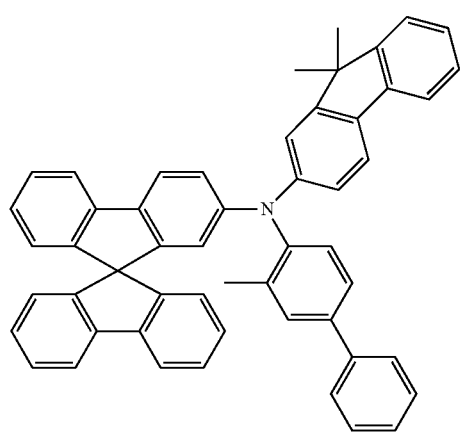
(55)
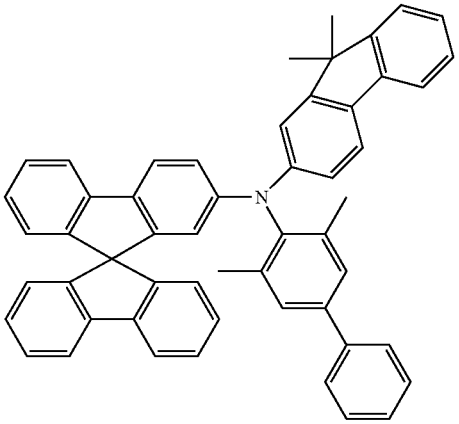
(56)
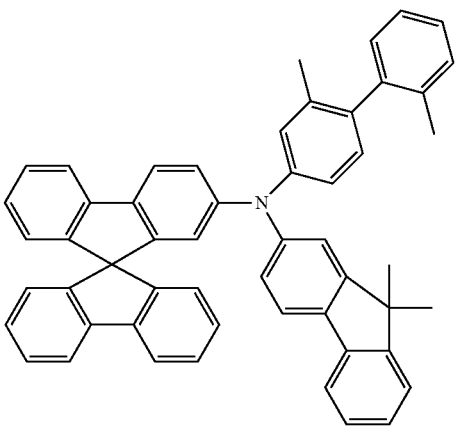
(57)
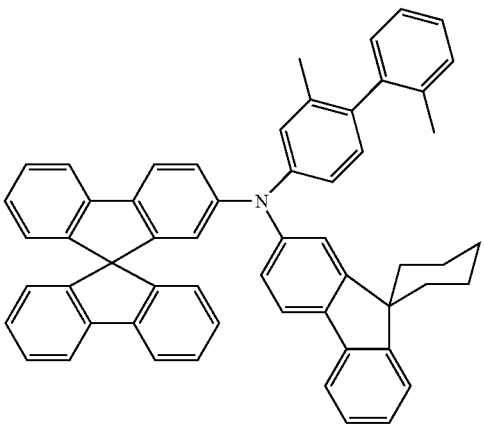
(58)

(59)
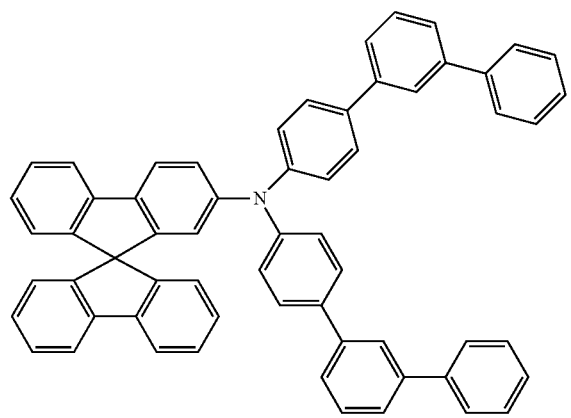
(60)
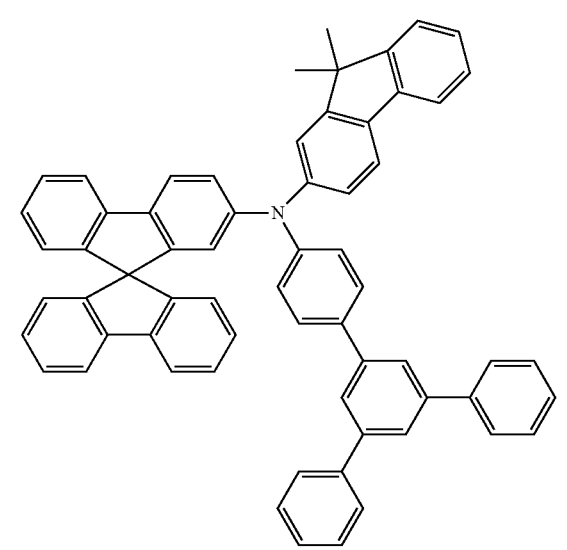
(61)
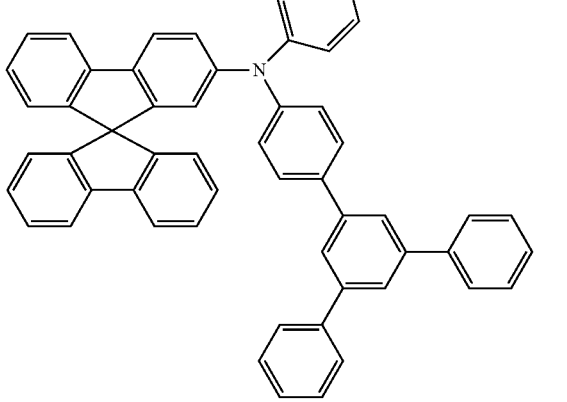
(62)
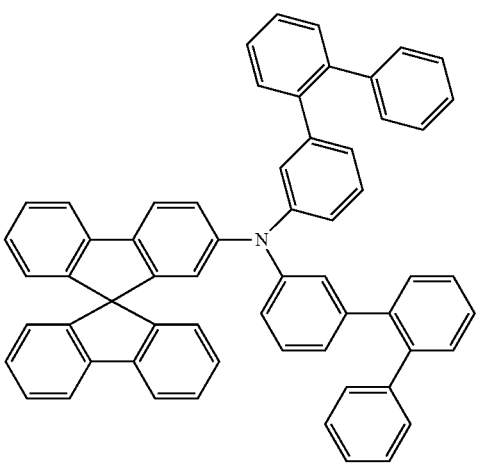
(63)
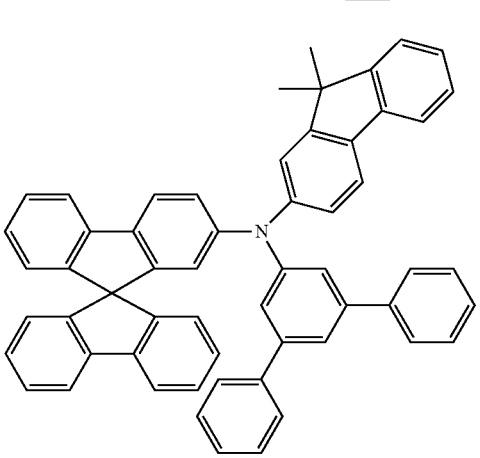
(64)
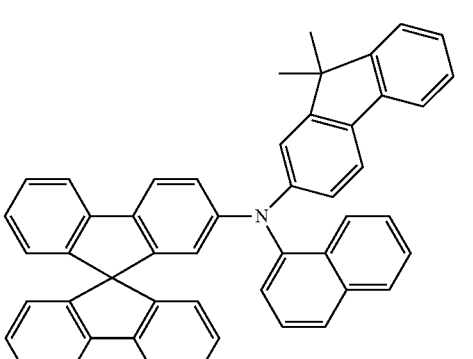
(65)
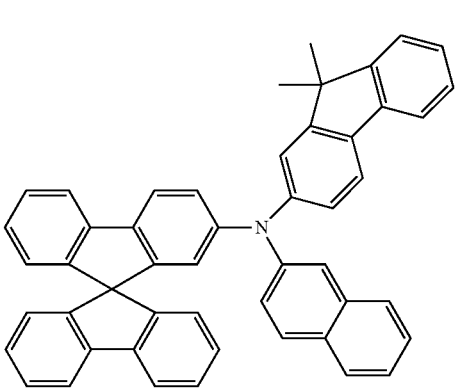

(66)
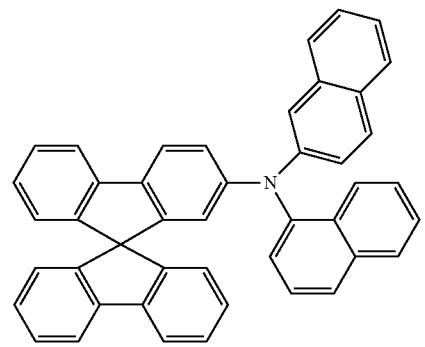
(67)
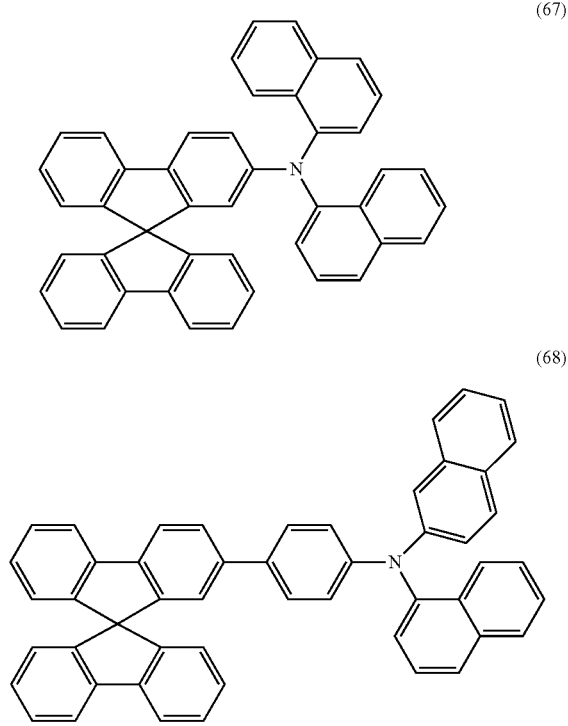
(68)
(69)
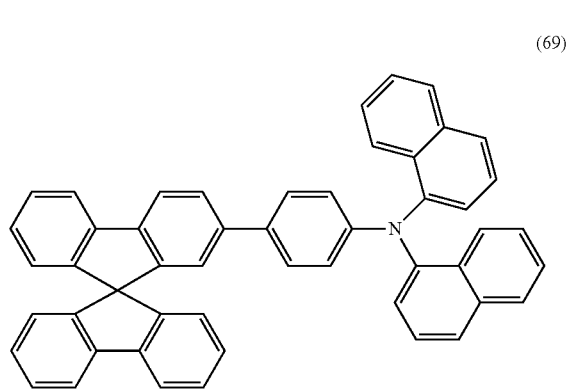
(70)
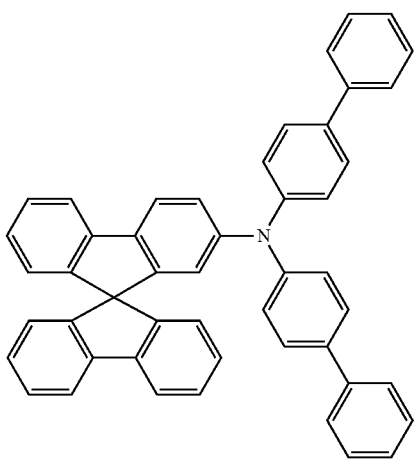
(71)
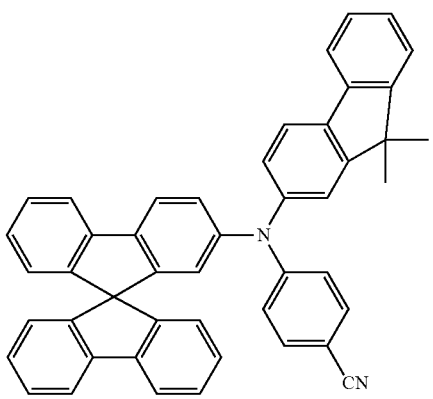
(72)
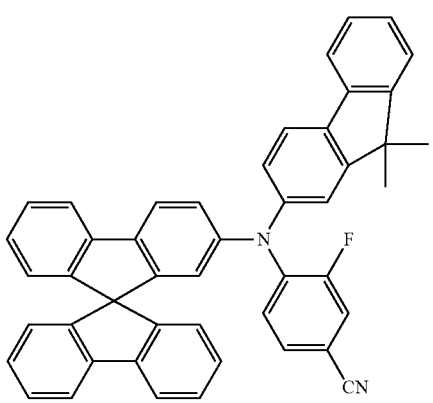

(73)
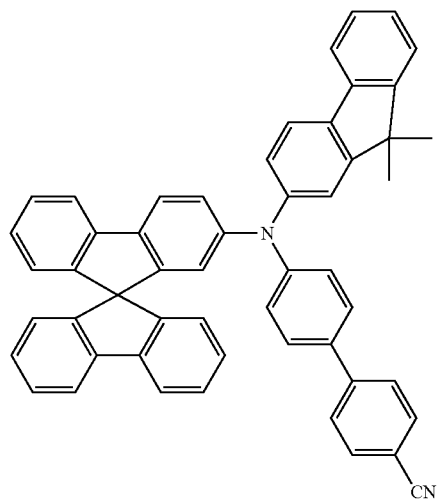
(76)
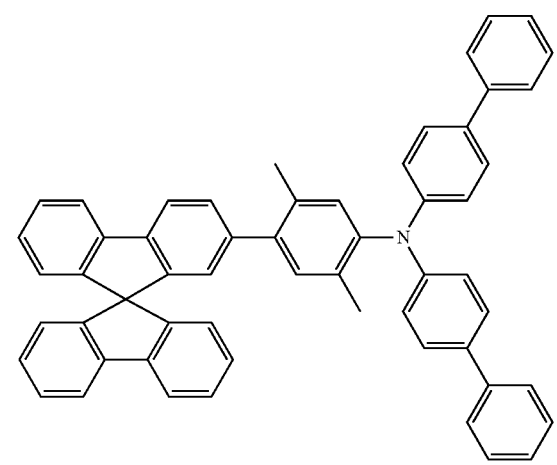
(74)
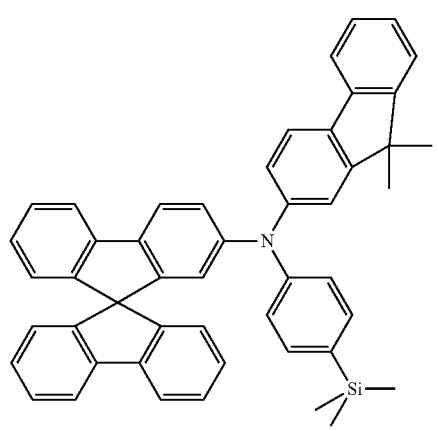
(77)
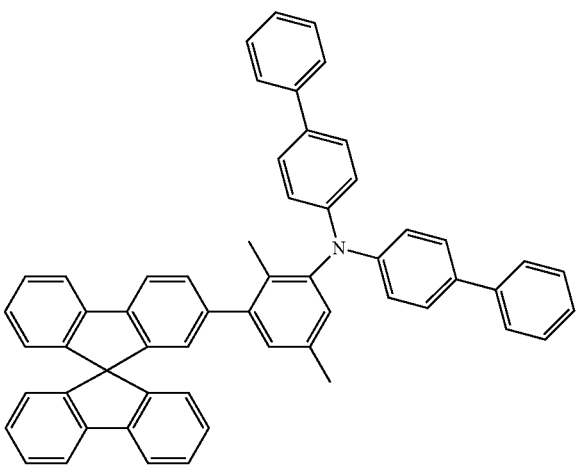
(75)
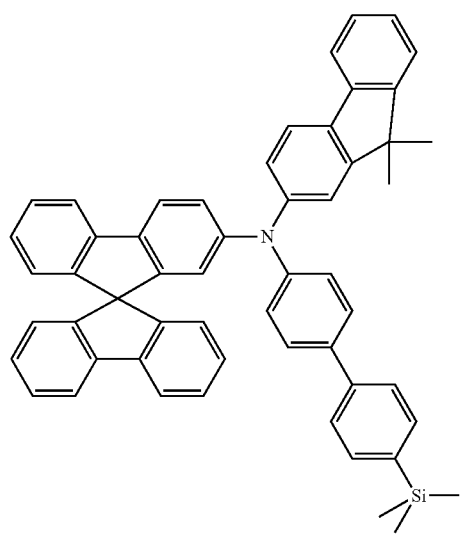
(78)
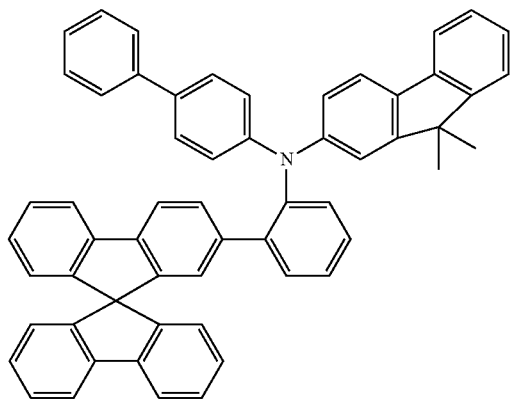

(79)
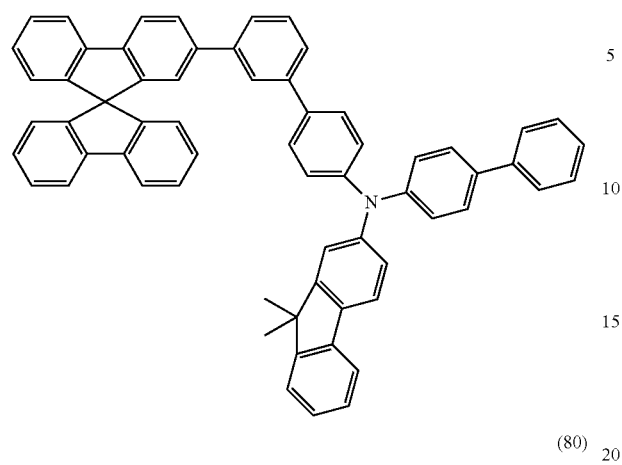
(83)
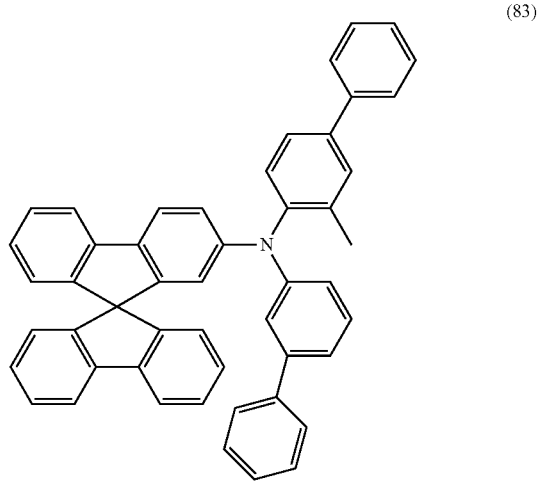
(80)
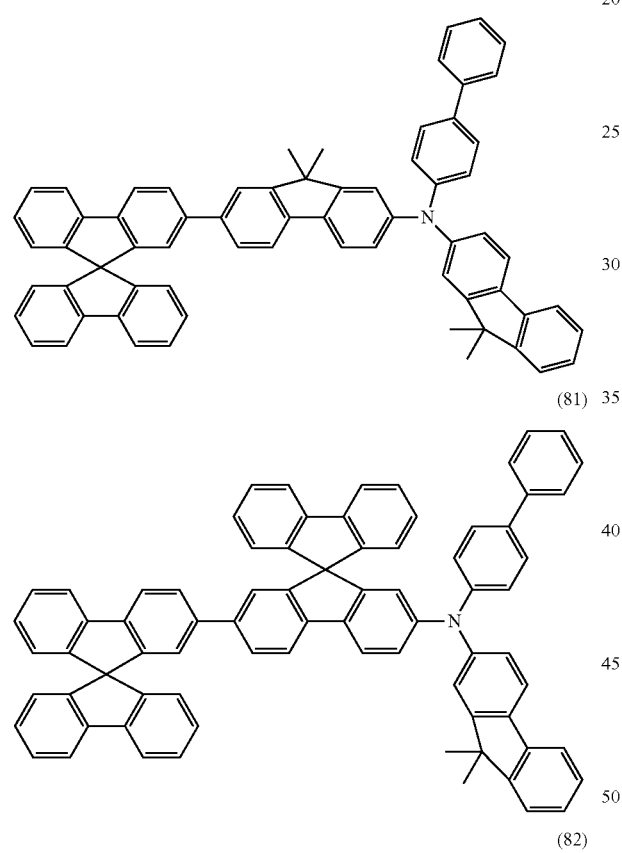
(84)
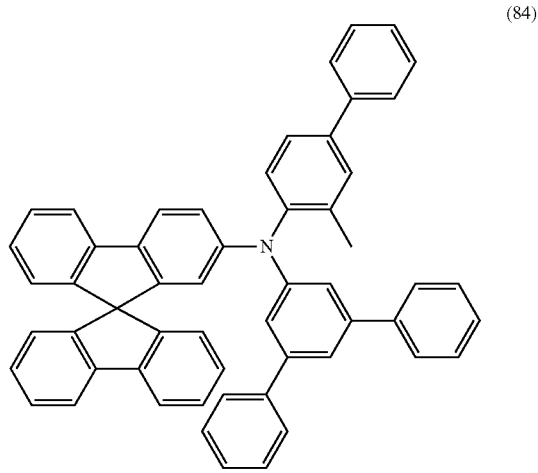
(81)
(82)
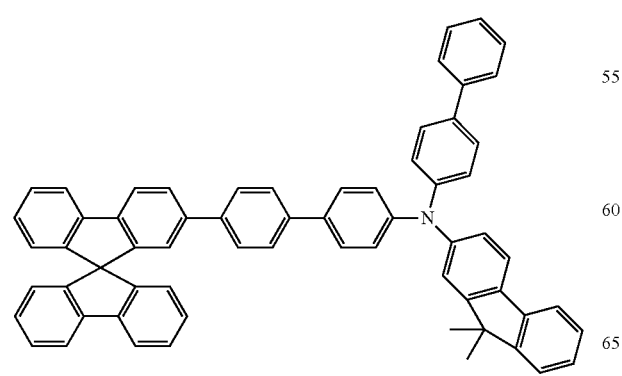
(85)
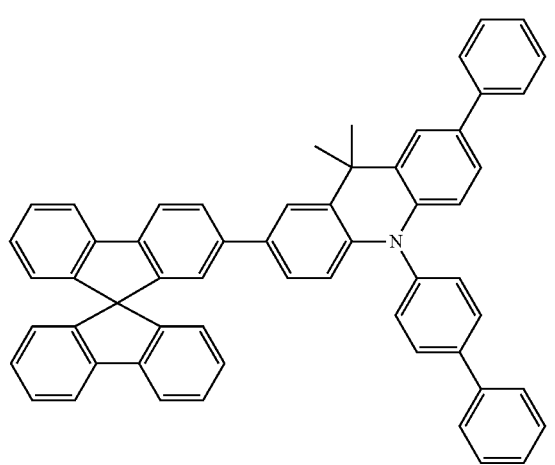

(86)
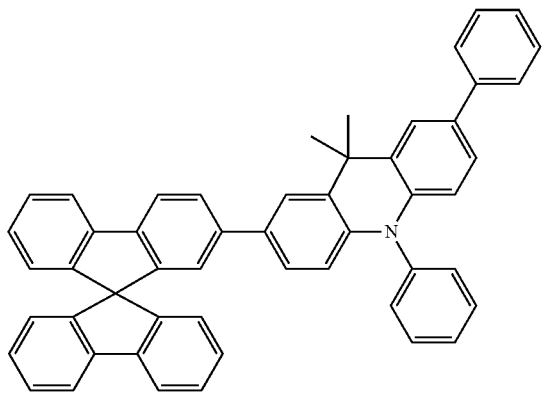
(87)
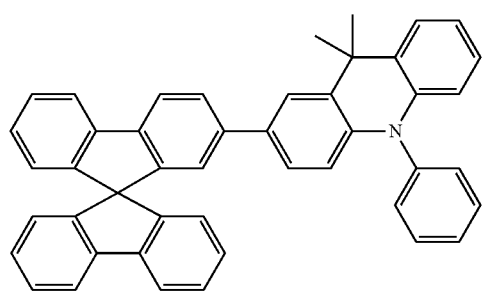
(88)
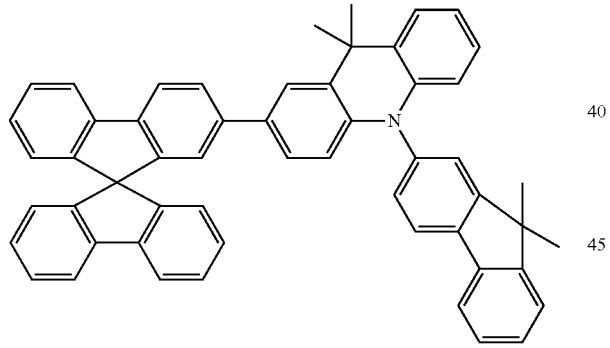
(89)
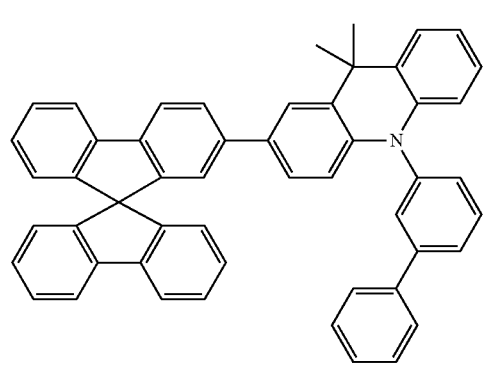
(90)
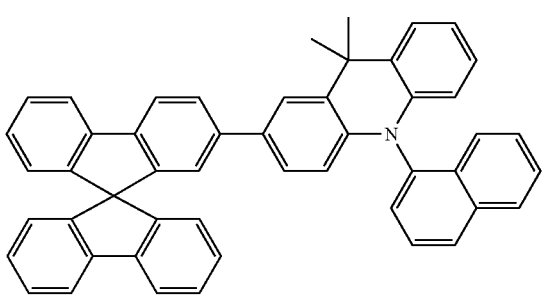
(91)
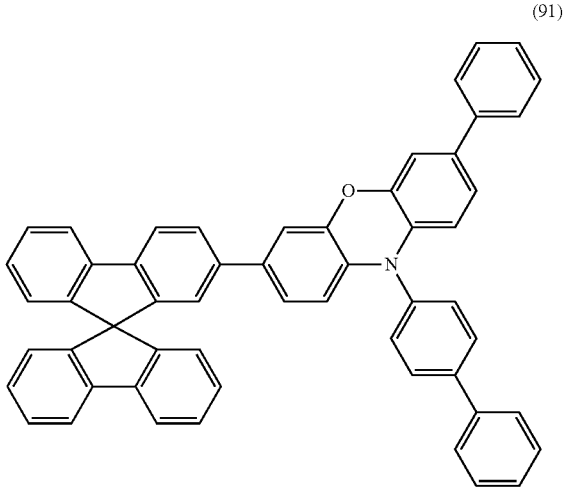
(92)
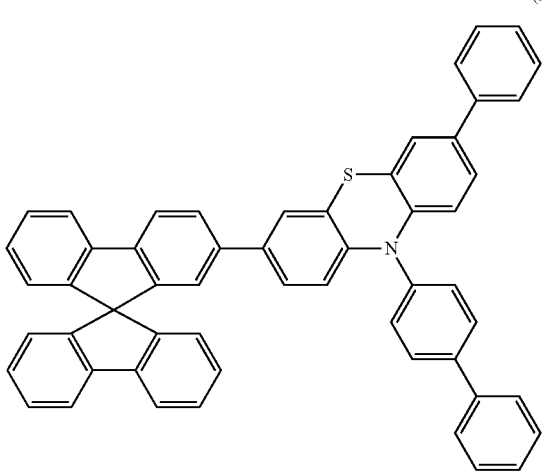

(93)
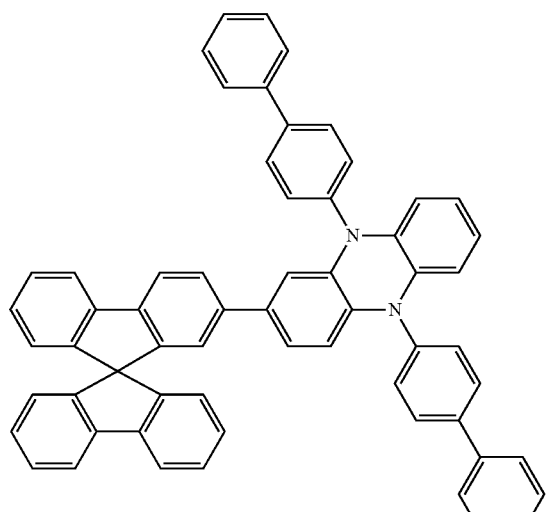
(94)
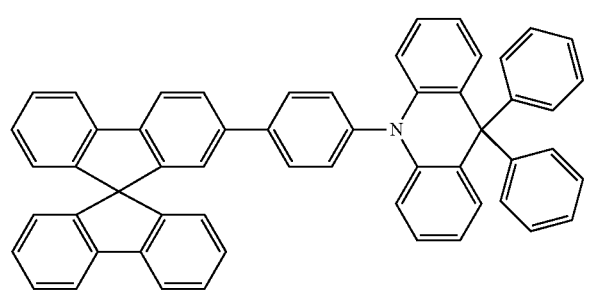
(95)
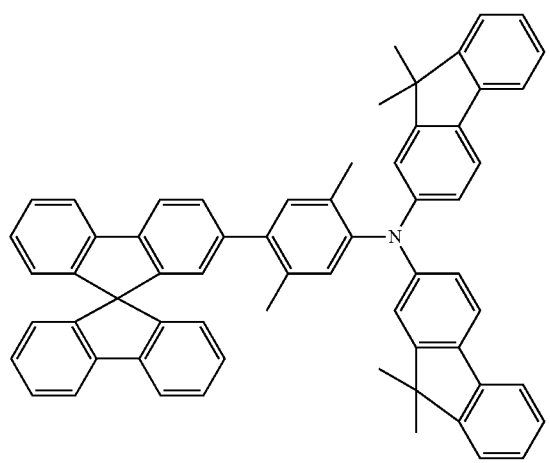
(97)
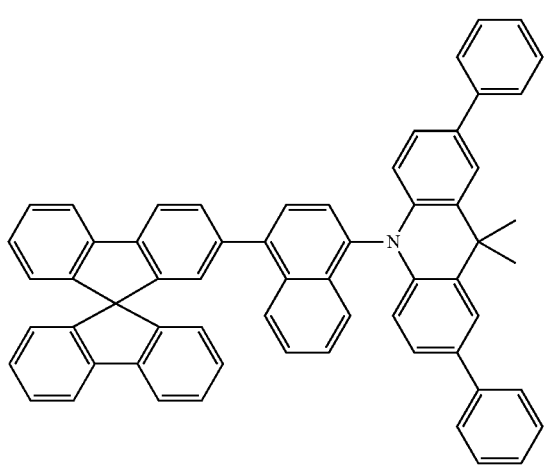
(98)
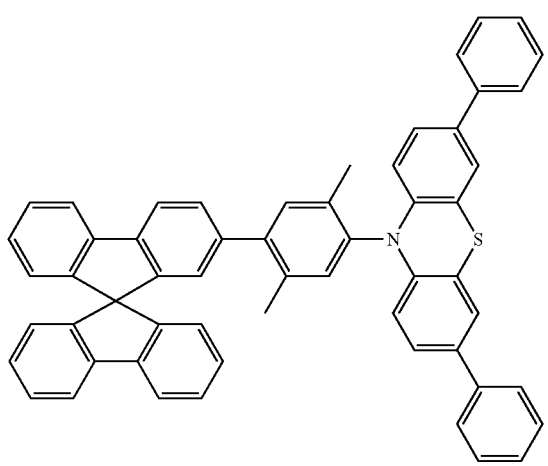
(99)
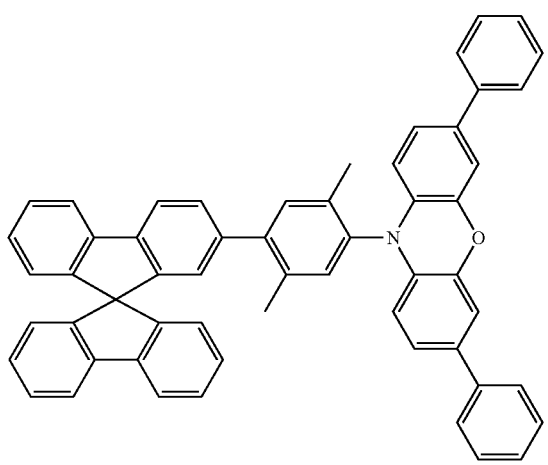

(100)
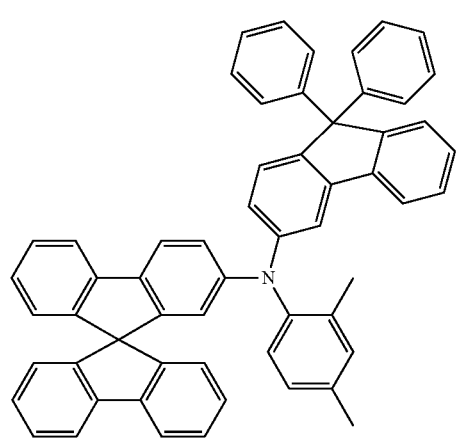
(101)
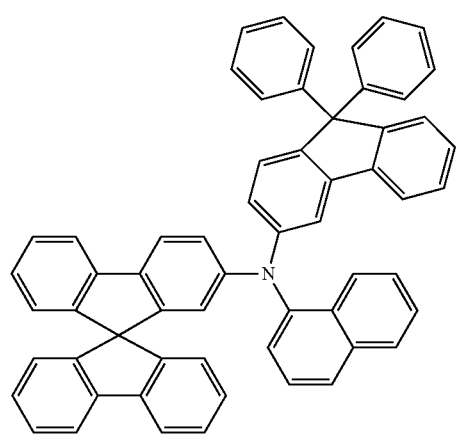
(102)
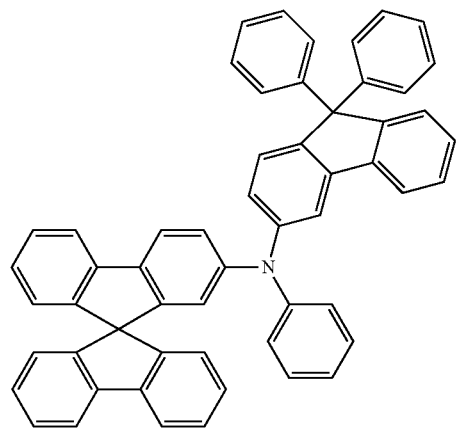
(103)
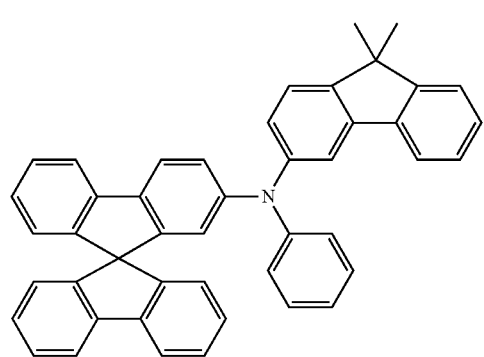
(104)
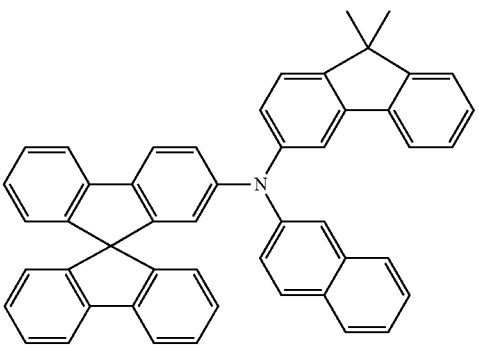
(105)
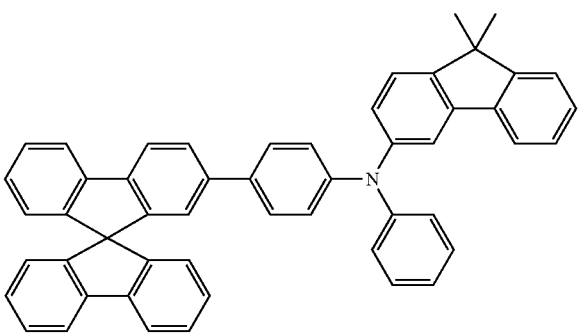
(106)
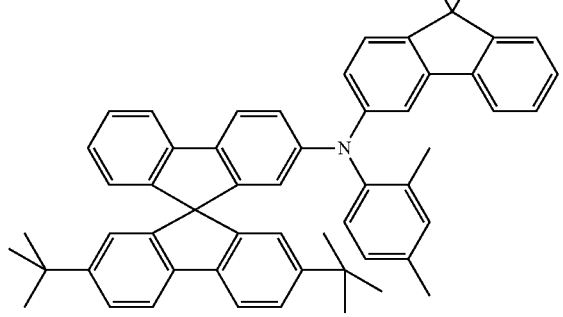
(107)
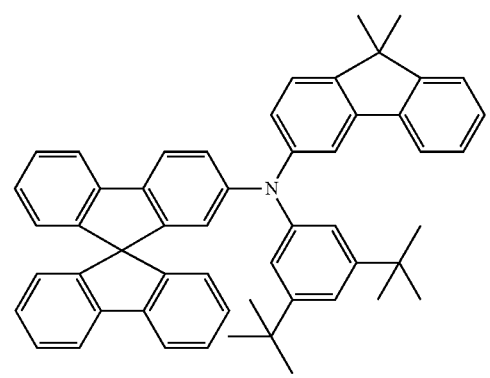

(108)
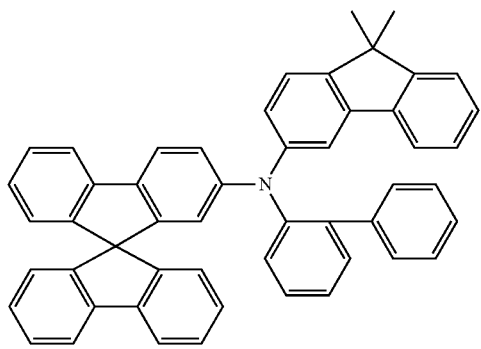
(109)
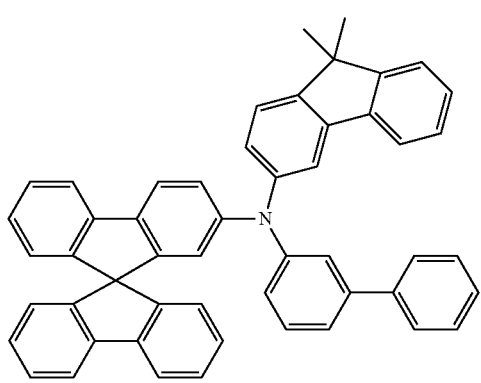
(110)
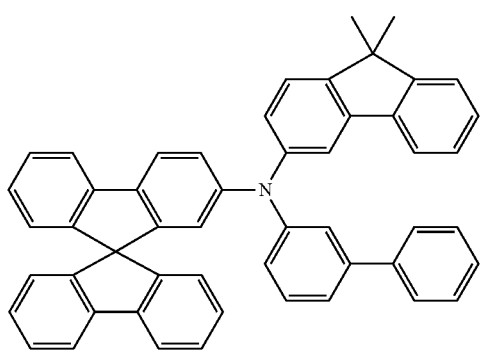
(111)
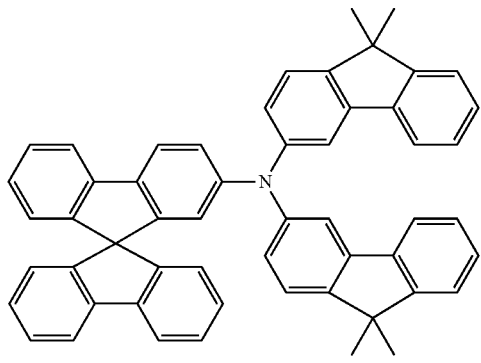
(112)
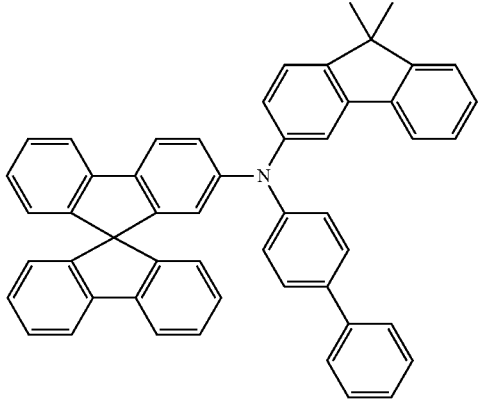
(113)
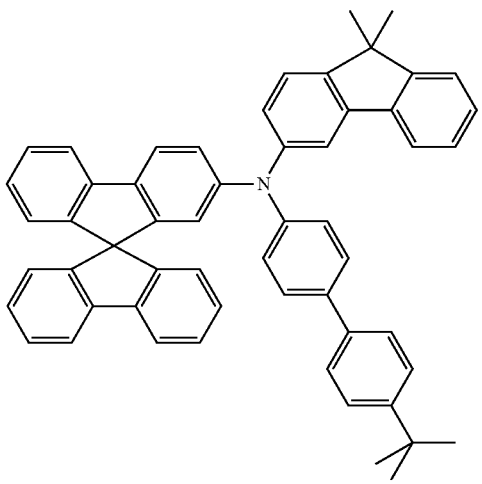
(114)
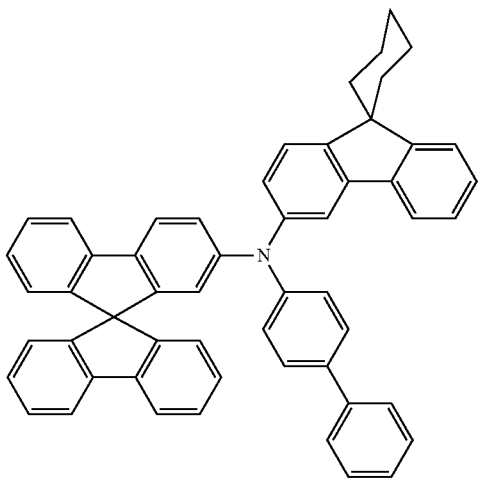

-continued
(115)
(116)
(117)
(118)
(119)
(120)
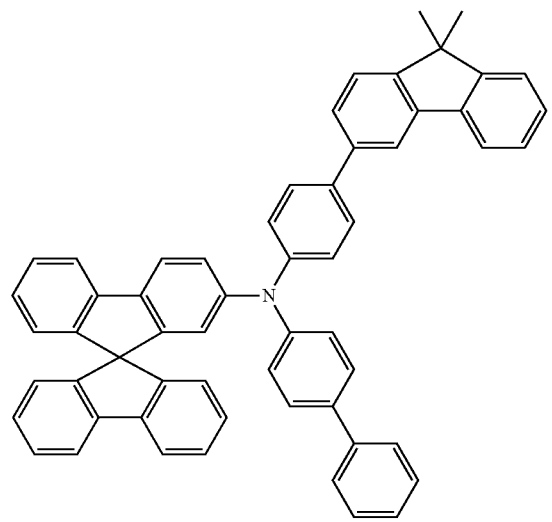
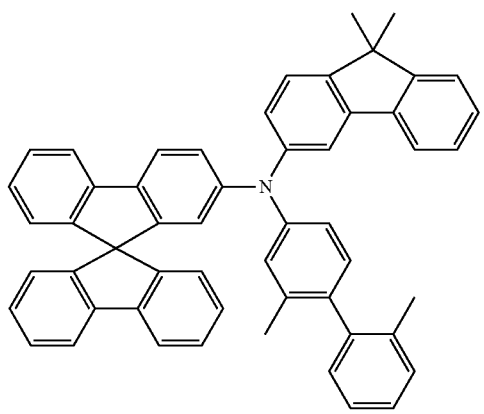
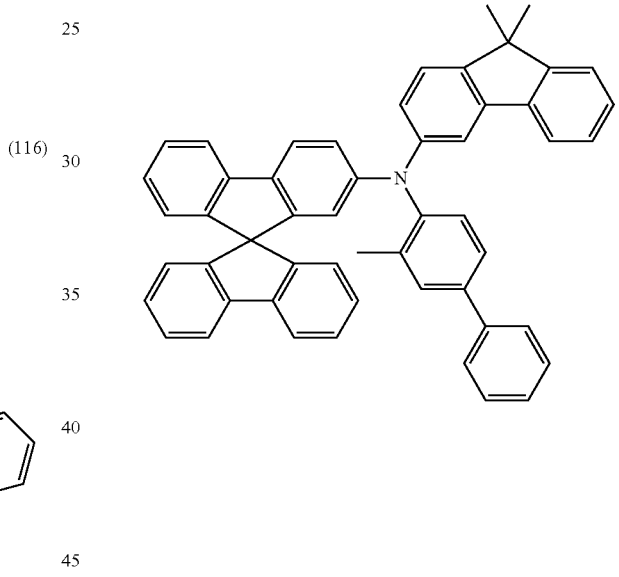
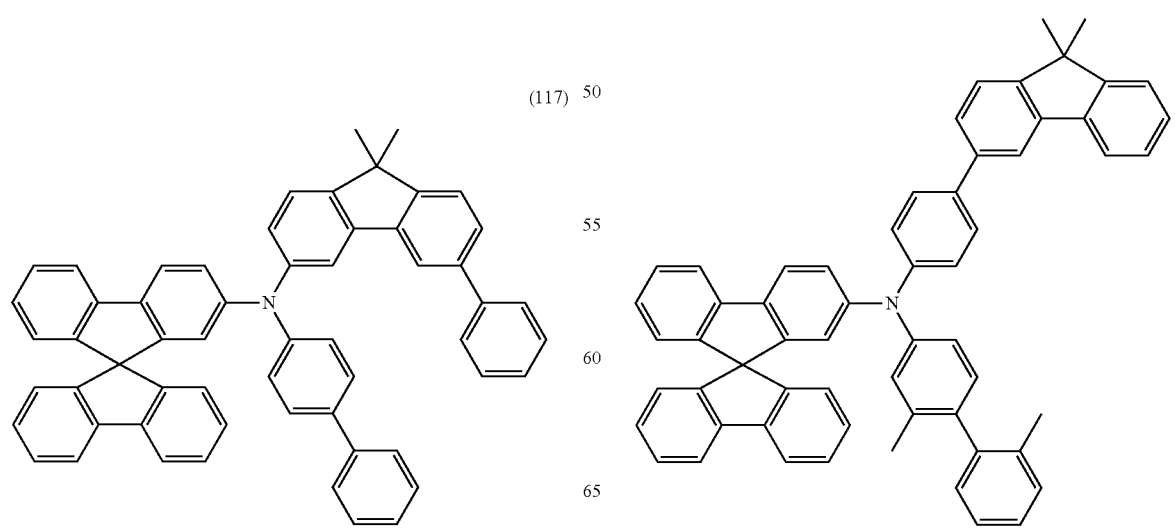

(121)
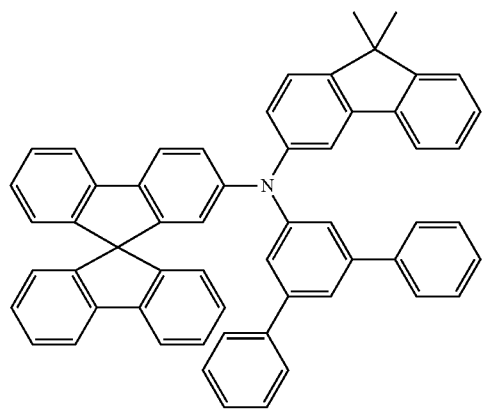
(122)
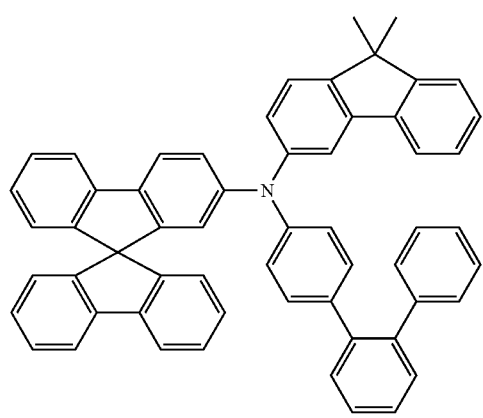
(123)
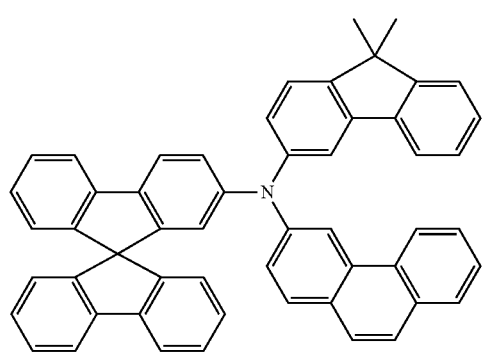
(124)
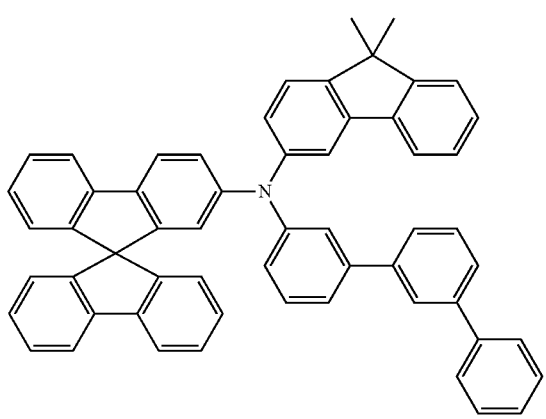
(125)
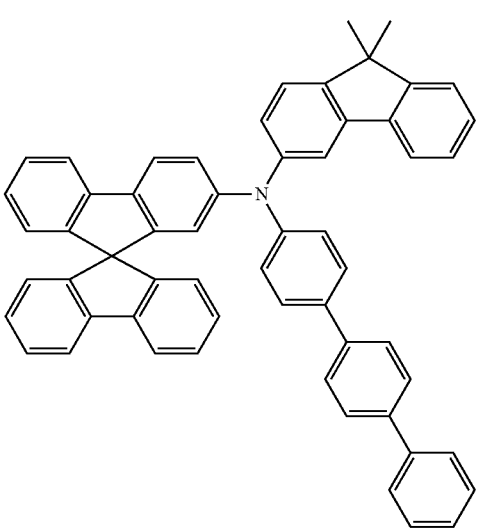
(126)
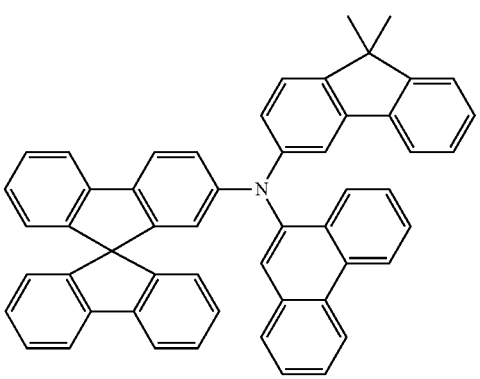
(127)
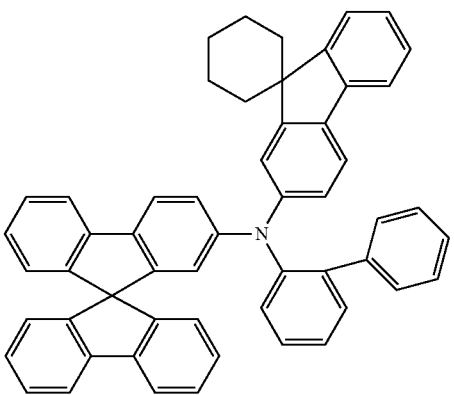

-continued
(128)
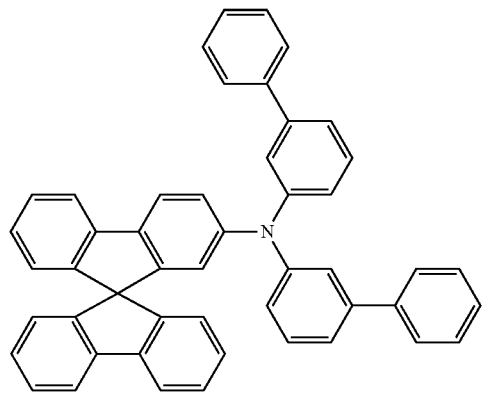
(129)
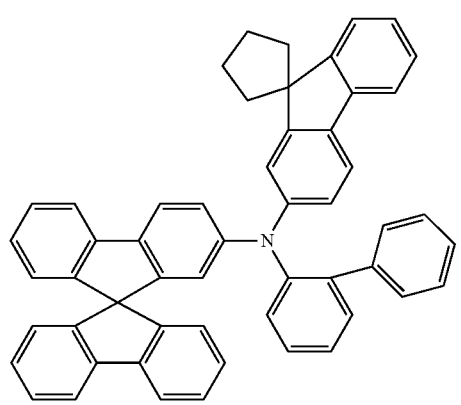
(130)
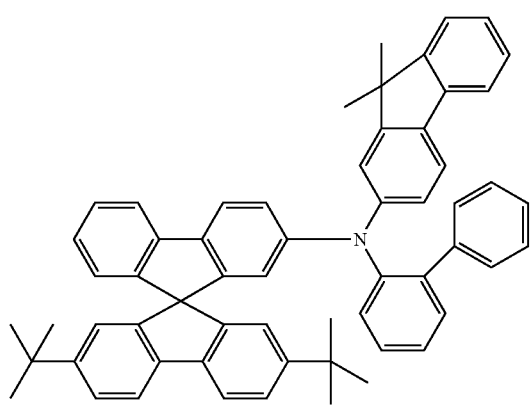
(131)
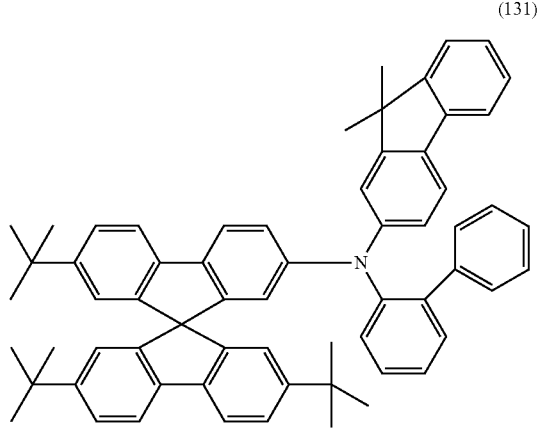
-continued
(132)
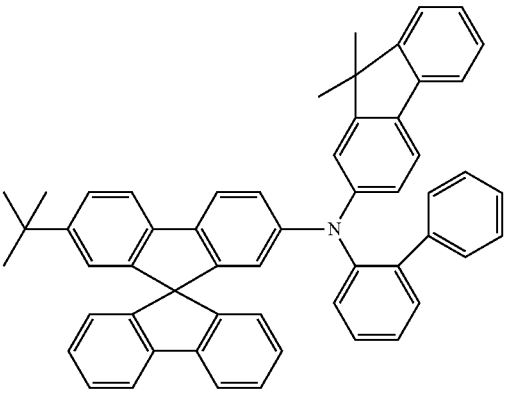
(133)
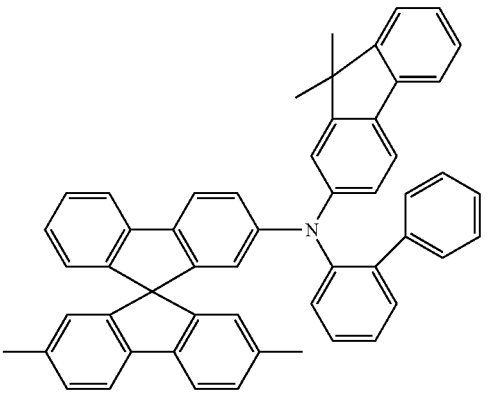
(134)
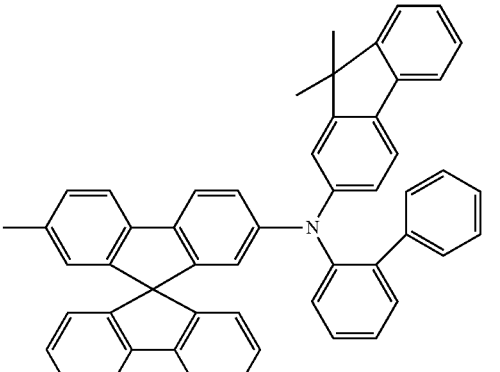
(135)
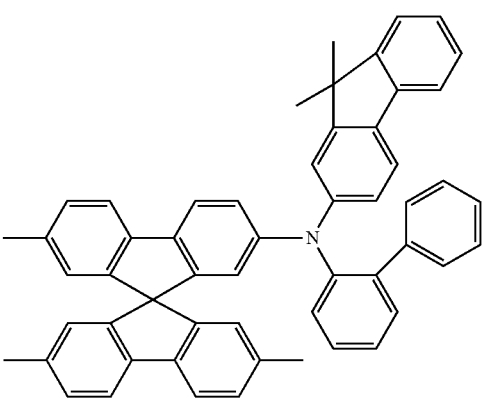

(136)
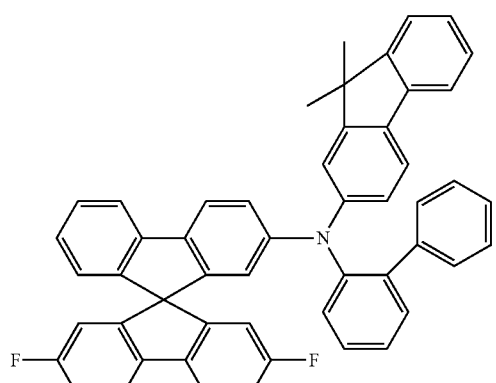
(137)
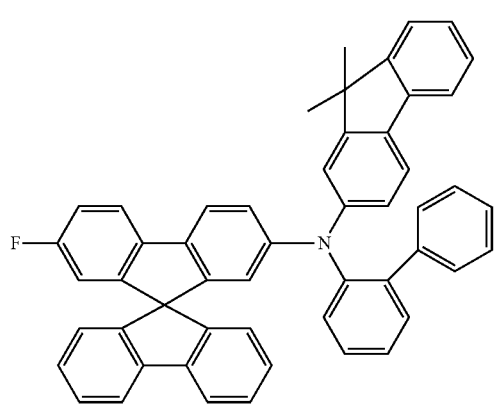
(138)
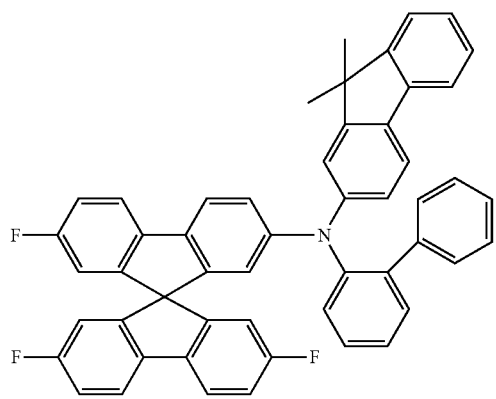
(139)
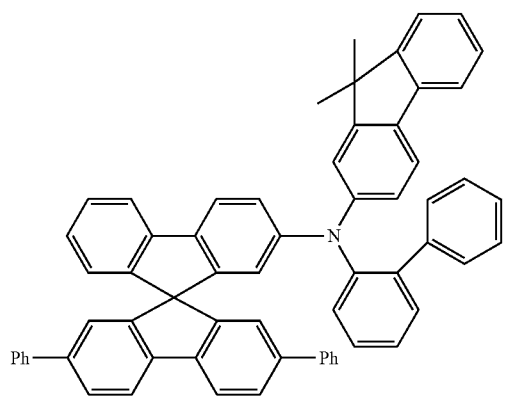
(140)
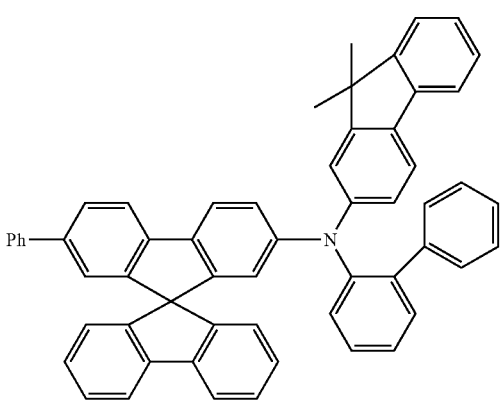
(141)
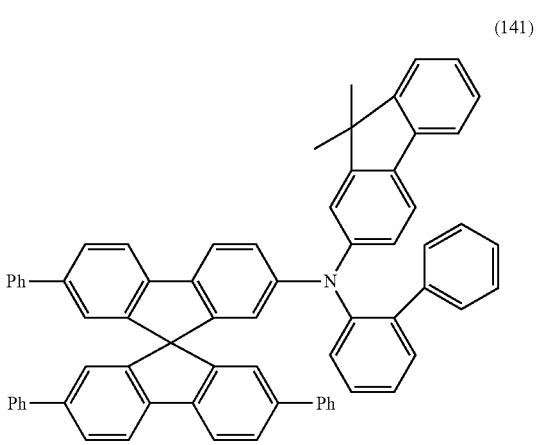
(142)
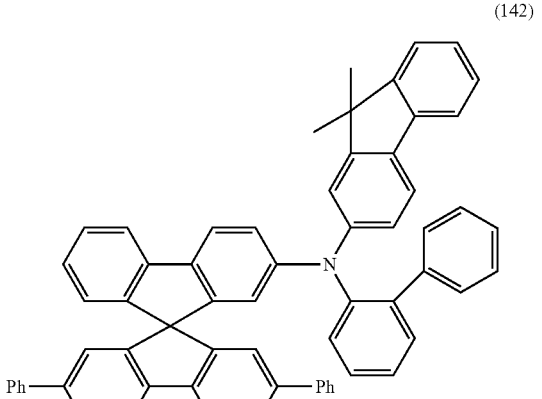

(143)
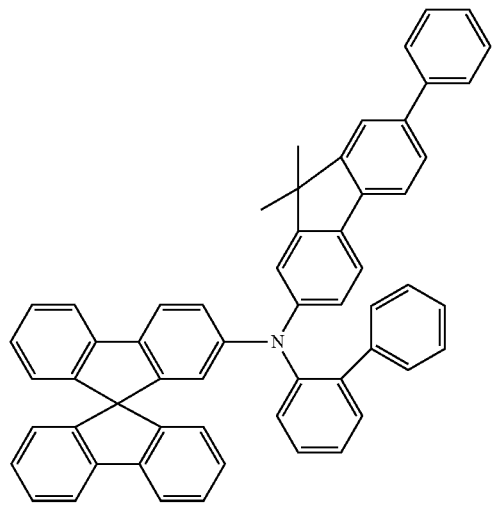
(144)
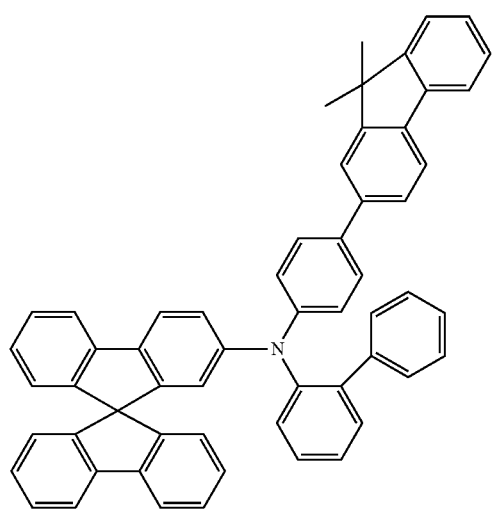
(145)
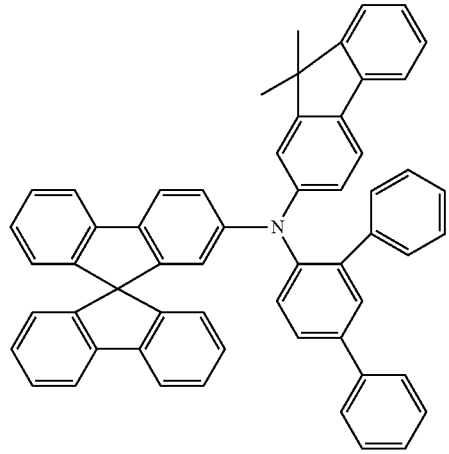
(146)
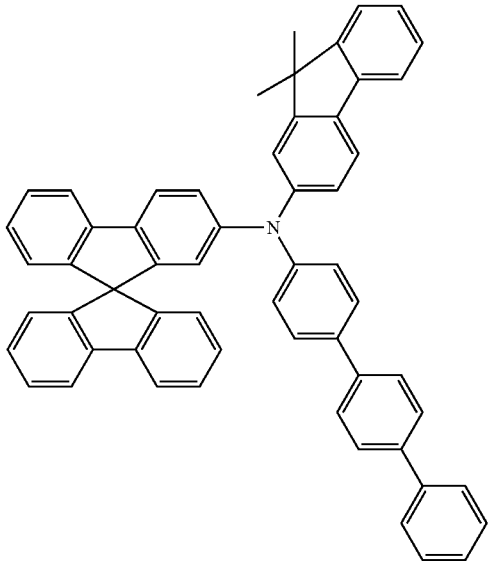
(147)
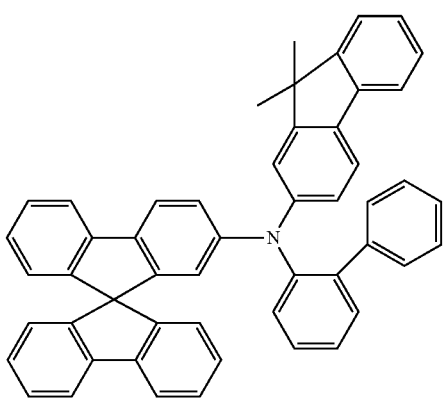
(148)
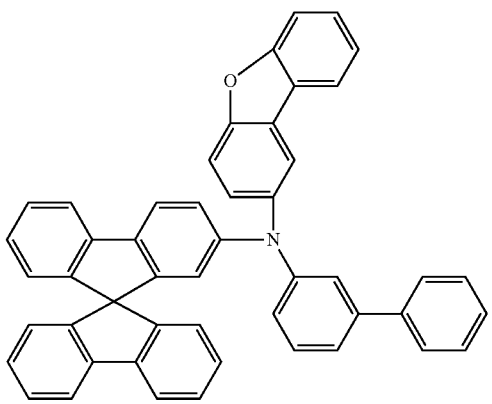

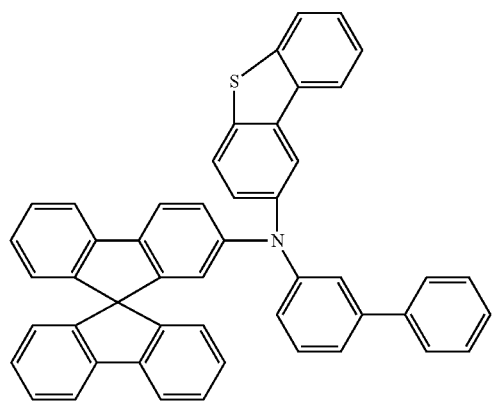
(149)
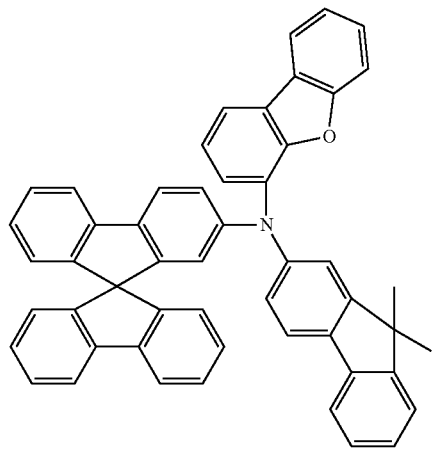
(152)
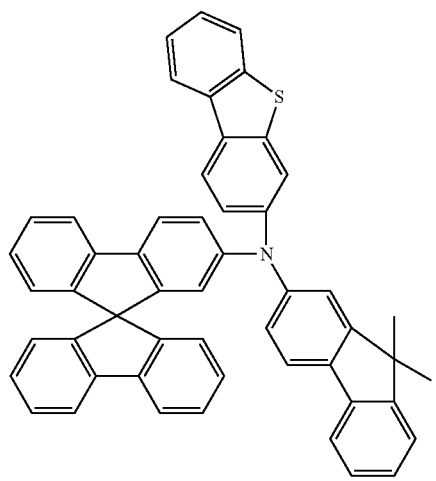
(150)
(153)
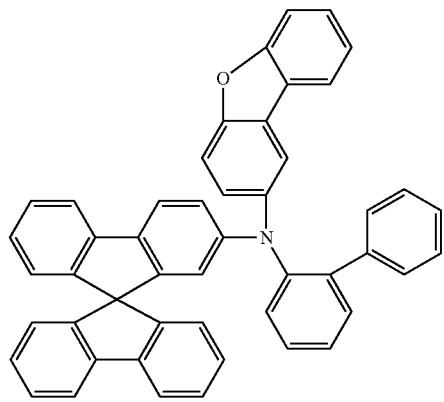
(151)
(154)

-continued
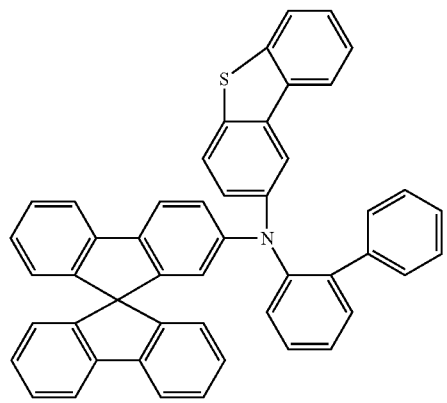
(155)
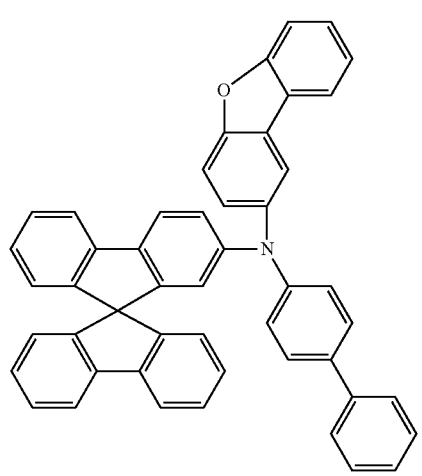
(156)
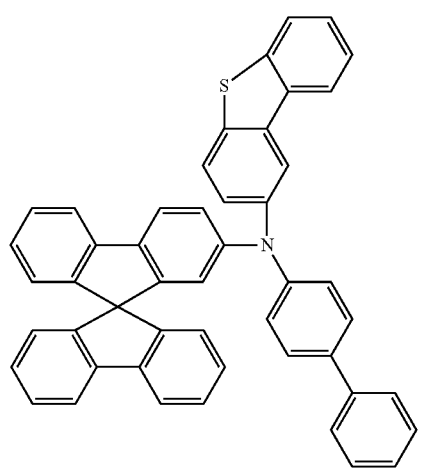
(157)
-continued
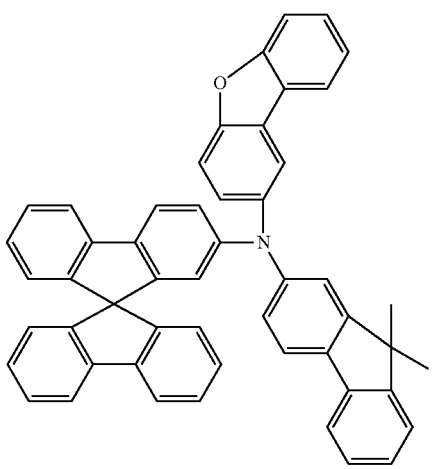
(158)
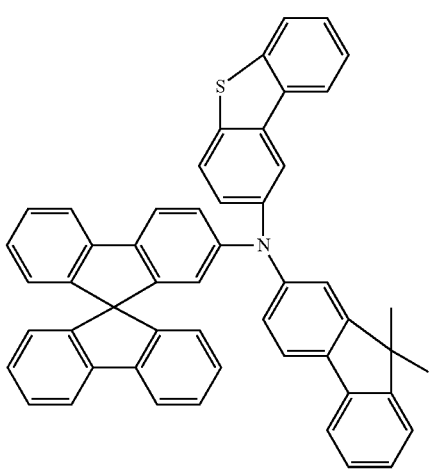
(159)
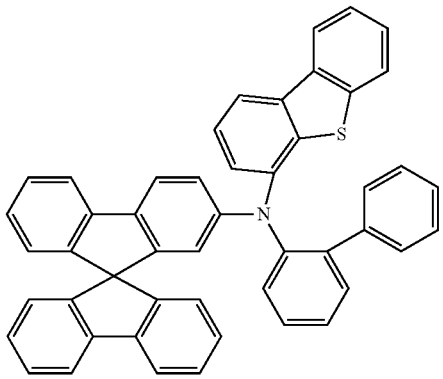
(160)

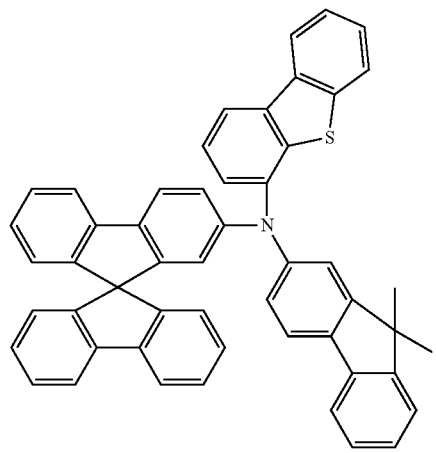
(161)
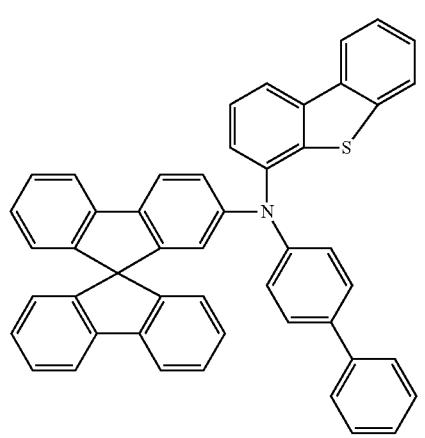
(162)
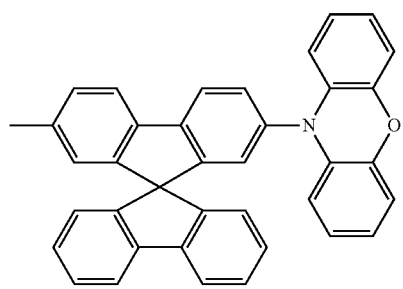
(163)
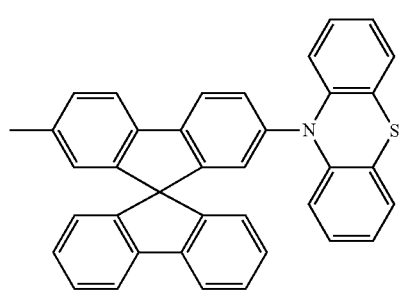
(164)
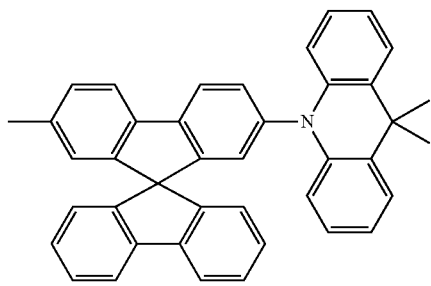
(165)
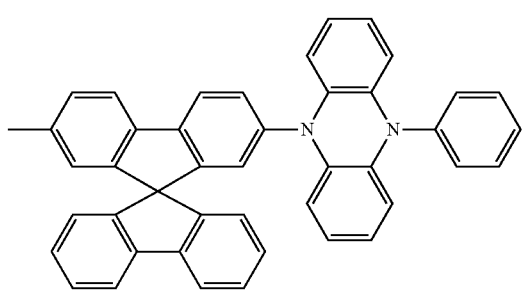
(166)
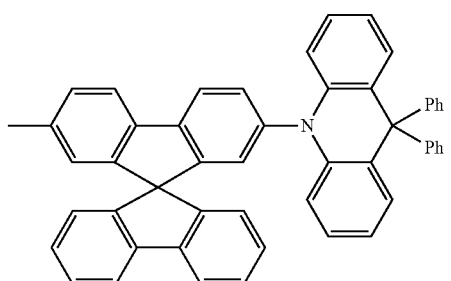
(167)
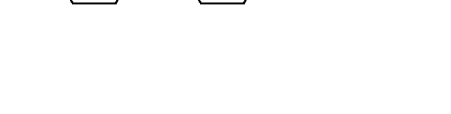
(168)
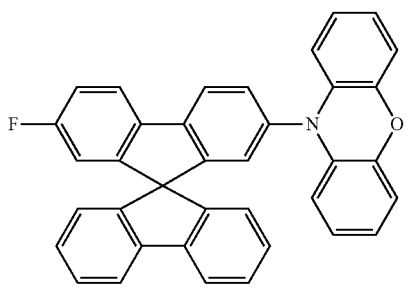
(168)
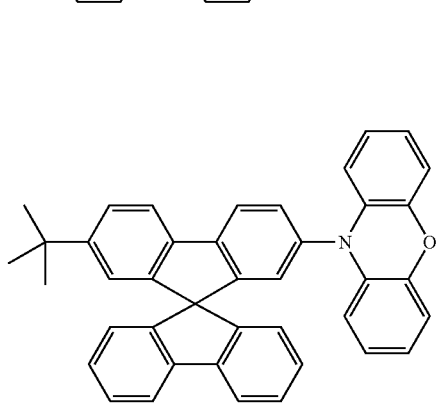
(169)

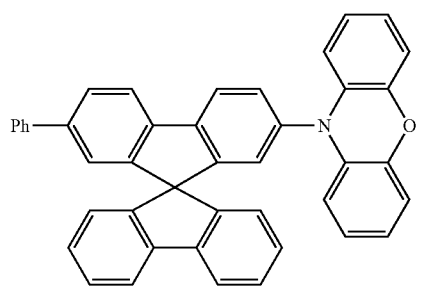
(170)
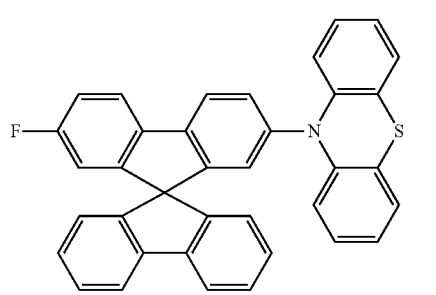
(171)
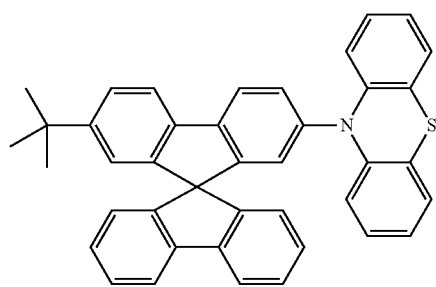
(172)
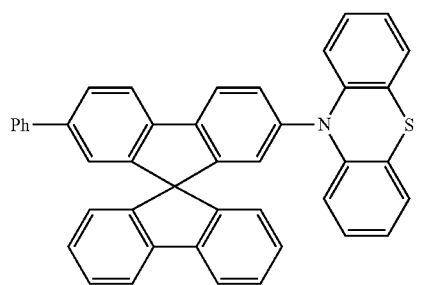
(173)
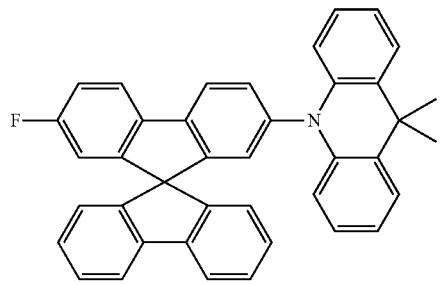
(174)
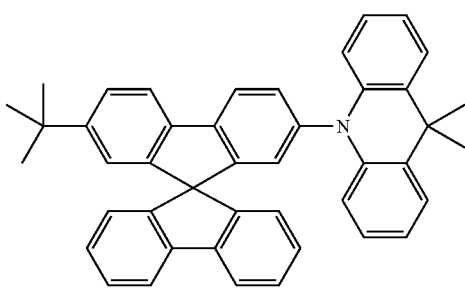
(175)
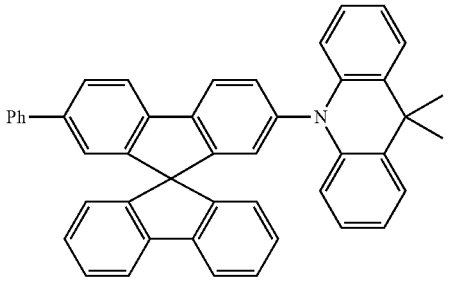
(176)
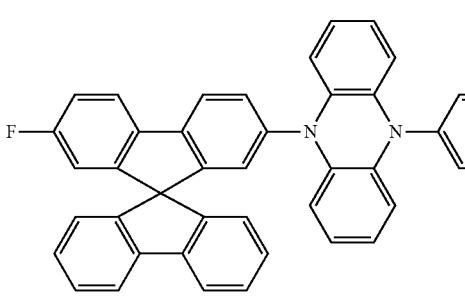
(177)
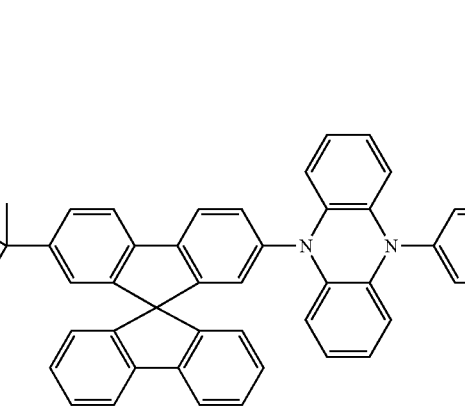
(178)
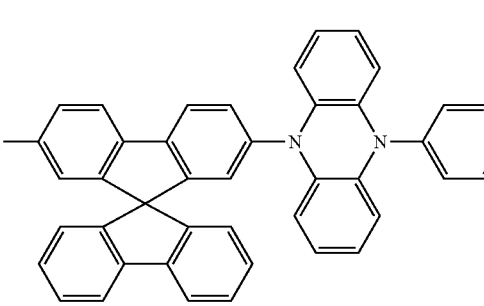
(179)

(180) 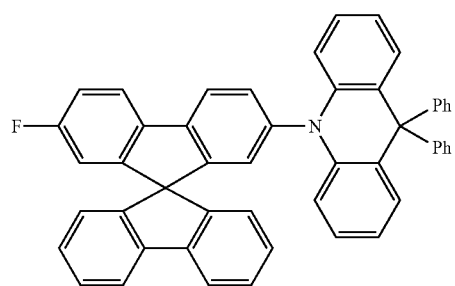
(181) 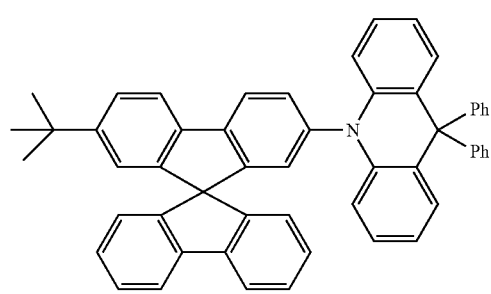
(182) 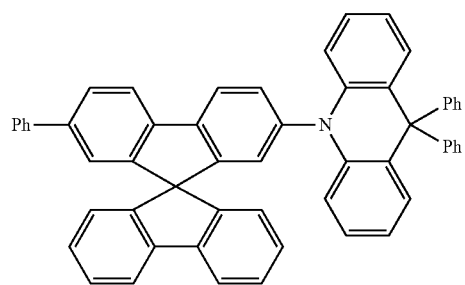
(183) 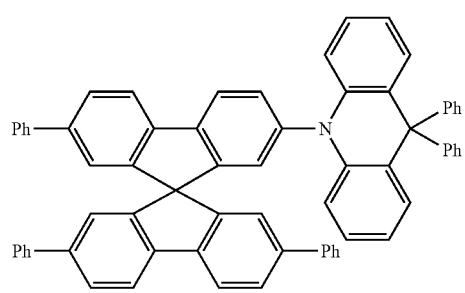
(184) 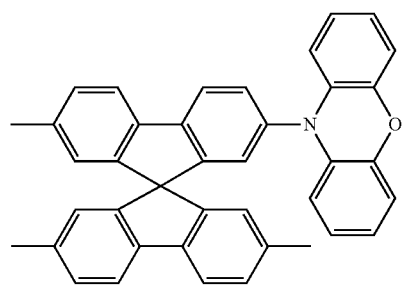
(185) 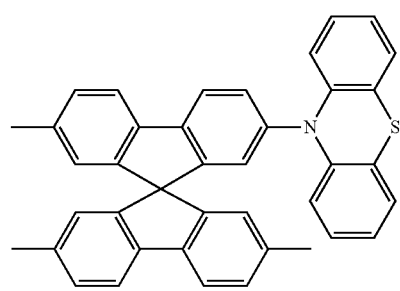
(186) 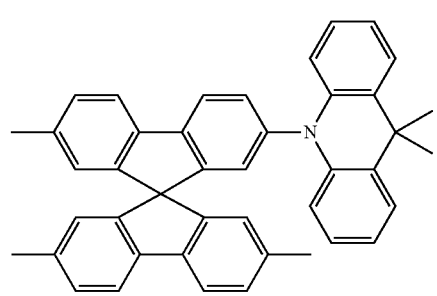
(187) 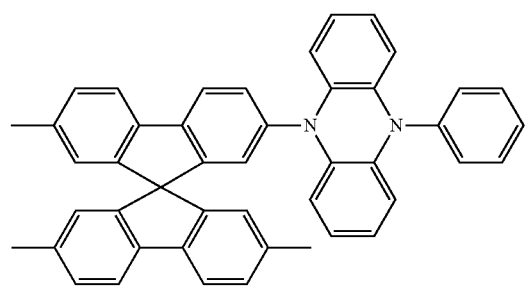
(188) 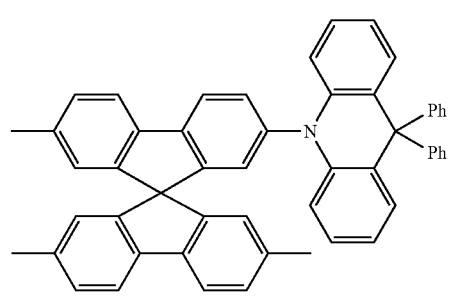
(189) 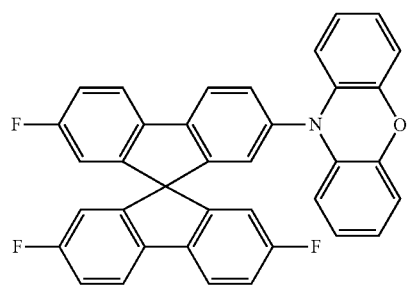

-continued
(190) 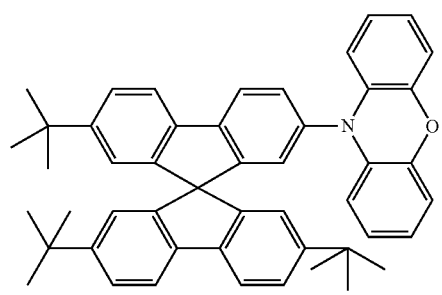
(191) 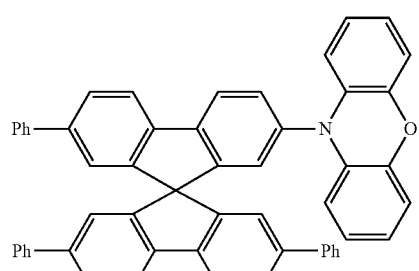
(192) 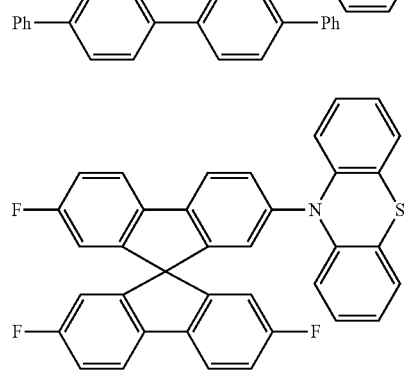
(193) 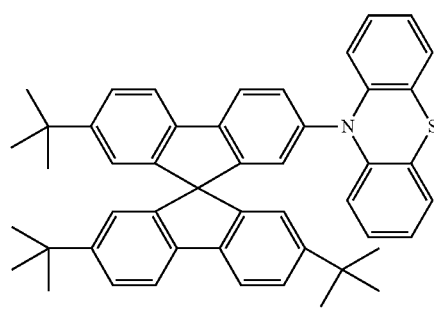
(194) 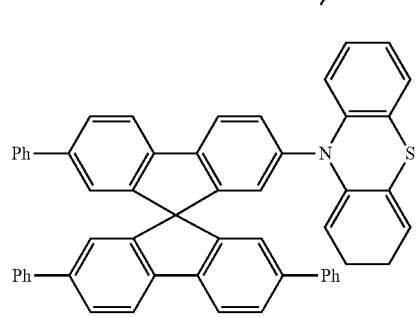
-continued
(195) 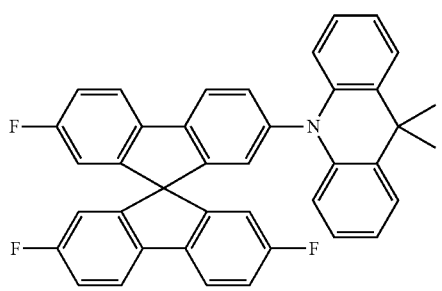
(196) 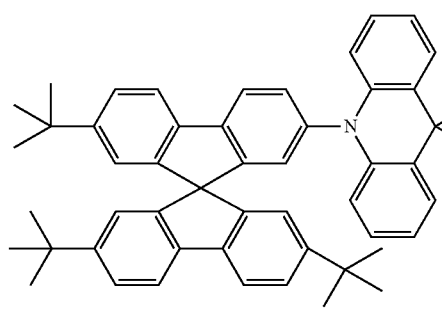
(197) 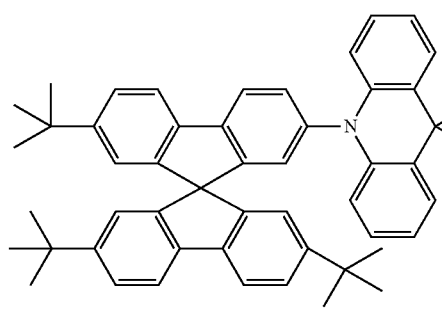
(198) 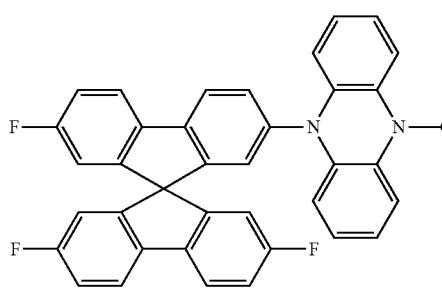
(199) 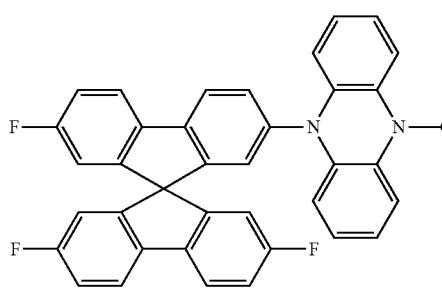

-continued (200)
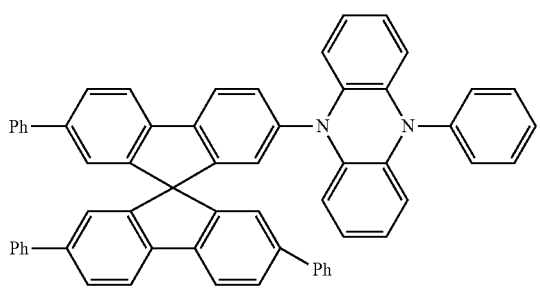

(201)
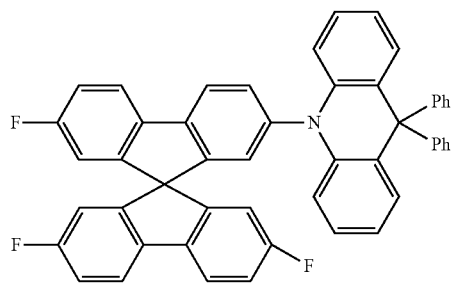

(202)
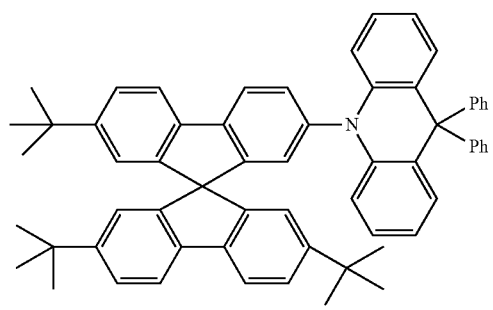

(203)
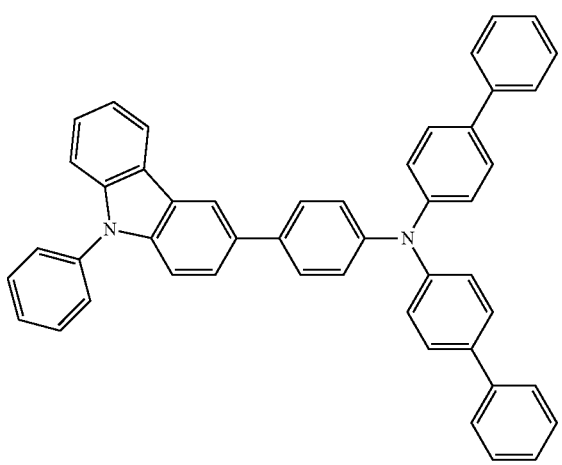

The electronic device according to the invention can comprise one or more emitting layers. The emitting layers can be fluorescent or phosphorescent, i.e. comprise fluorescent or phosphorescent emitters.

The term phosphorescent emitters (dopants) typically encompasses compounds in which the light emission takes place through a spin-forbidden transition, for example a transition from an excited triplet state or a state having a relatively high spin quantum number, for example a quintet state.

Suitable phosphorescent emitters are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent dopants used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present invention, all luminescent iridium, platinum or copper complexes are regarded as phosphorescent compounds.

Examples of the phosphorescent dopants described above are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used in accordance with the prior art for phosphorescent OLEDs and as are known to the person skilled in the art in the area of organic electroluminescent devices are suitable for use in the devices according to the invention. The person skilled in the art will also be able to employ further phosphorescent complexes without inventive step in combination with the compounds according to the invention in OLEDs.

Preferred fluorescent emitters for use in the electronic devices according to the invention are selected from the class of the triarylamine compounds, as defined above. At least one of the aryl or heteroaryl groups bonded to the nitrogen atom is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred dopants are indenofluorenamines and indenofluorenediamines, for example in accordance with WO 2006/108497 or WO 2006/122630, benzoindenofluorenamines and benzoindenofluorenediamines, for example in accordance with WO 2008/006449, and dibenzoindenofluorenamines and dibenzoindenofluorenediamines, for example in accordance with WO 2007/140847, as well as the indenofluorene derivatives containing condensed aryl groups disclosed in WO 2010/012328. Preference is likewise given to the pyrenearylamines disclosed in WO 2012/048780 and the as yet unpublished EP 12004426.8. Preference is likewise given to the benzoindenofluorenamines disclosed in the as yet unpublished EP 12006239.3 and the benzofluorenamines disclosed in the as yet unpublished EP 13000012.8.

The emitting layer preferably comprises one or more host materials (matrix materials) and one or more dopant materials (emitter materials).

According to a preferred embodiment, an emitting layer comprises a plurality of matrix materials (mixed-matrix systems) and/or a plurality of dopants. In this case too, the dopants are generally the materials whose proportion in the system is the smaller and the matrix materials are the materials whose proportion in the system is the greater. In individual cases, however, the proportion of an individual matrix material in the system may be smaller than the proportion of an individual dopant.

In mixed-matrix systems, one of the two matrix materials is preferably a material having hole-transporting properties and the other material is a material having electron-transporting properties. The desired electron-transporting and hole-transporting properties of the mixed-matrix components may, however, also be mainly or completely combined in a single mixed-matrix component, where the further mixed-matrix component or mixed-matrix components fulfil(s) other functions. The two different matrix materials may be present here in a ratio of 1:50 to 1:1, preferably 1:20 to 1:1, particularly preferably 1:10 to 1:1 and very particularly preferably 1:4 to 1:1. Preference is given to the use of mixed-matrix systems in phosphorescent organic electroluminescent devices. Preferred embodiments of mixed-matrix systems are disclosed, inter alia, in the application WO 2010/108579.

The mixed-matrix systems may include one or more dopants, preferably one or more phosphorescent dopants. In general, mixed-matrix systems are preferably employed in phosphorescent emitting layers.

Preferred matrix materials for fluorescent emitters are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Preferred matrix materials for phosphorescent emitters are aromatic ketones, aromatic phosphine oxides or aromatic sulfoxides or sulfones, for example in accordance with WO 2004/013080, WO 2004/093207, WO 2006/005627 or WO 2010/006680, triaryiamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109, WO 2011/000455 or WO 2013/041176, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or WO 2012/143080, triphenylene derivatives, for example in accordance with WO 2012/048781, or lactams, for example in accordance with WO 2011/116865 or WO 2011/137951.

The electronic device according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where at least one of these layers preferably comprises at least one compound of the formula (I) and where the three layers exhibit blue, green and orange or red emission (for the basic structure see, for example, WO 2005/011013). Alternatively and/or additionally, the compounds according to the invention may also be present in the hole-transport layer or in another layer. It should be noted that, for the generation of white light, an emitter compound used individually which emits in a broad wavelength range may also be suitable instead of a plurality of emitter compounds which emit in colours.

The cathode of the electronic device according to the invention preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ba/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

Besides anode, cathode, emitting layer and hole-transport layers A, B, C and optionally hole-transport layer A', the electronic device according to the invention preferably also comprises further functional layers.

The sequence of the layers of the electronic device is preferably the following: anode/hole-transport layer A'/hole-transport layer A/hole-transport layer B/hole-transport layer C/emitting layer/electron-transport layer/electron-injection layer/cathode.

All of the said layers do not have to be present, and/or further layers may be present in addition to the said layers.

These additional layers are preferably selected from hole-injection layers, hole-transport layers, electron-blocking layers, emitting layers, interlayers, electron-transport layers, electron-injection layers, hole-blocking layers, exciton-blocking layers, charge-generation layers, p/n junctions and coupling-out layers.

The electronic device according to the invention preferably has at least one electron-transport layer, which is arranged between emitting layer and cathode, where the electron-transport layer preferably comprises at least one n-dopant and at least one electron-transport material matrix.

An n-dopant is taken to mean a compound which is able to at least partially reduce the other compound present in the layer (the matrix) and in this way increases the conductivity of the layer. n-Dopants in accordance with the present application are typically electron-donor compounds or strong reducing agents. n-Dopants which can be used are, for example, the materials disclosed in Chem. Rev, 2007, 107, pp. 1233 ff., Section 2.2, such as alkali metals, alkaline-earth metals and electron-rich and readily oxidisable organic compounds or transition-metal complexes.

Furthermore, the electronic device according to the invention preferably has at least one electron-injection layer, which is arranged between electron-transport layer and cathode. The electron-injection layer is preferably directly adjacent to the cathode.

The materials used for the electron-transport layer and electron-injection layer can be all materials as are used in accordance with the prior art as electron-transport materials in the electron-transport layer. In particular, aluminium complexes, for example $Alq_3$, zirconium complexes, for example $Zrq_4$, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives are suitable. Furthermore suitable materials are derivatives of the above-mentioned compounds, as disclosed in JP 2000/053957, WO 2003/060956, WO 2004/028217, WO 2004/080975 and WO 2010/072300.

During production, the device is preferably structured, provided with contacts and finally sealed in order to exclude water and/or air.

In a preferred embodiment, the electronic device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

It is likewise preferred for one or more layers in the electronic device according to the invention to be coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

It is likewise preferred for one or more layers in the electronic device according to the invention to be produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing.

It is furthermore preferred, for the production of the electronic device according to the invention, to apply one or more layers from solution and one or more layers by a sublimation process.

The electronic devices according to the invention can be employed in displays, as light sources in lighting applications and as light sources in medical and/or cosmetic applications (for example phototherapy).

WORKING EXAMPLES

Part A: Determination of the HOMO Positions of Compounds

The HOMO positions of the materials are determined via quantum-chemical calculations. To this end, use is made of the "Gaussian03W" software package (Gaussian Inc.). In order to calculate organic substances without metals, firstly a geometry optimisation is carried out using the "Ground State/Semi-empirical/Default Spin/AM1/Charge 0/Spin Singlet" method. An energy calculation is subsequently carried out on the basis of the optimised geometry. The "TD-SFC/DFT/Default Spin/B3PW91" method with the "6-31G(d)" base set is used here (Charge 0, Spin Singlet). The energy calculation gives the HOMO HEh in hartree units. The HOMO values in electron-volts calibrated with reference to cyclic voltammetry measurements are determined therefrom as follows:

HOMO (eV)=(($HEh$*27.212)−0.9899)/1.1206

These values are to be regarded as the HOMO of the materials in the sense of this application.

Table with HOMO data for the compounds used (structures see below)

| Material | HOMO |
|---|---|
| HIM1/HTM1 | −5.25 eV |
| HIM 2 | −4.85 eV |
| NPB | −5.16 eV |
| HTM2 | −5.43 eV |
| HTM3 | −5.23 eV |
| HTM4 | −5.35 eV |
| HTM5 | −5.32 eV |
| HTM6 | −5.23 eV |

Part B: Production of OLEDs

OLEDs according to the invention and OLEDs in accordance with the prior art are produced by a general process in accordance with WO 04/058911, which is adapted to the circumstances described here (layer-thickness variation, materials).

The data for various OLEDs are presented in the following Examples E1 to E13 according to the invention and in the reference Examples V1-V11. The substrates used are glass plates coated with structured ITO (indium tin oxide) in a thickness of 50 nm. The OLEDs basically have the following layer structure: substrate/p-doped hole-transport layer A' (HIL1)/hole-transport layer A (HTL)/p-doped hole-transport layer B (HIL2)/hole-transport layer C (EBL)/emission layer (EML)/electron-transport layer (ETL)/electron-injection layer (EIL) and finally a cathode. The cathode is formed by an aluminium layer with a thickness of 100 nm. The materials required for the production of the OLEDs are shown in Table 1, the structure of the various electronic devices produced is shown in Table 2.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by co-evaporation. An expression such as H1:SEB1 (5%) here means that material H1 is present in the layer in a proportion by volume of 95% and SEB1 is present in the layer in a proportion of 5%. Analogously, the electron-transport layer or the hole-injection layers may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordinates are calculated therefrom. The expression EQE @ 10 mA/cm$^2$ denotes the external quantum efficiency at a current density of 10 mA/cm$^2$. LT80 @ 60 mA/cm$^2$ is the lifetime by which the ° LED has dropped to 80% of the initial intensity at an initial luminance at constant current of 60 mA/cm$^2$.

TABLE 1

Structures of the materials used

F4TCNQ

HIM1

TABLE 1-continued

Structures of the materials used

HIM2

H1

SEB1

SEB2

TABLE 1-continued
Structures of the materials used
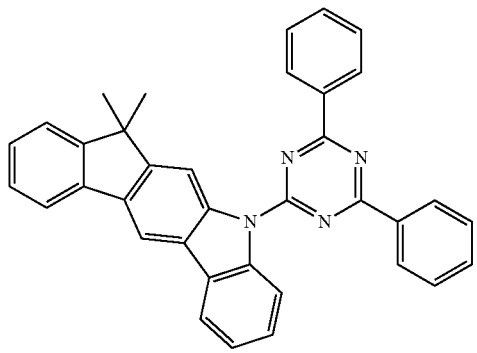 [SMILES: CC1(C)c2ccccc2-c2cc3c4ccccc4n(-c4nc(-c5ccccc5)nc(-c5ccccc5)n4)c3cc21]
H2
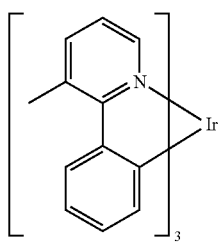
TEG
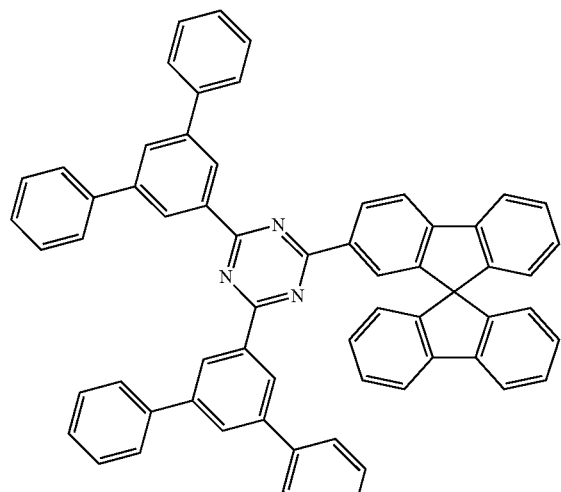
ETM
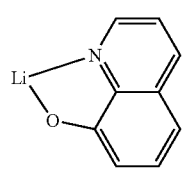
LiQ
TABLE 1-continued
Structures of the materials used
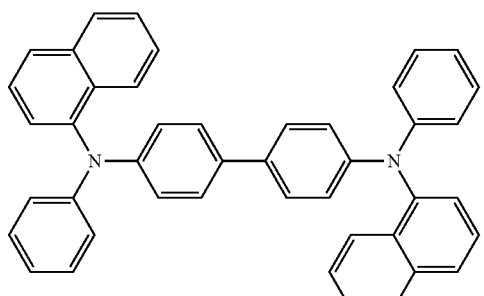
NPB
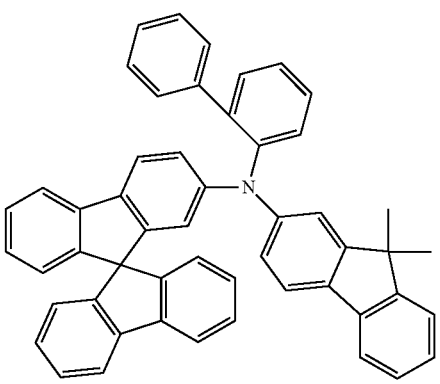 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
HTM1
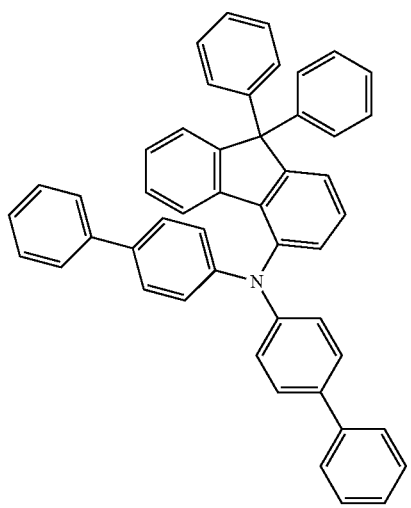 [SMILES: c1ccc(-c2ccc(N(c3ccc(-c4ccccc4)cc3)c3cccc4c3-c3ccccc3C4(c3ccccc3)c3ccccc3)cc2)cc1]
HTM2

TABLE 1-continued
Structures of the materials used
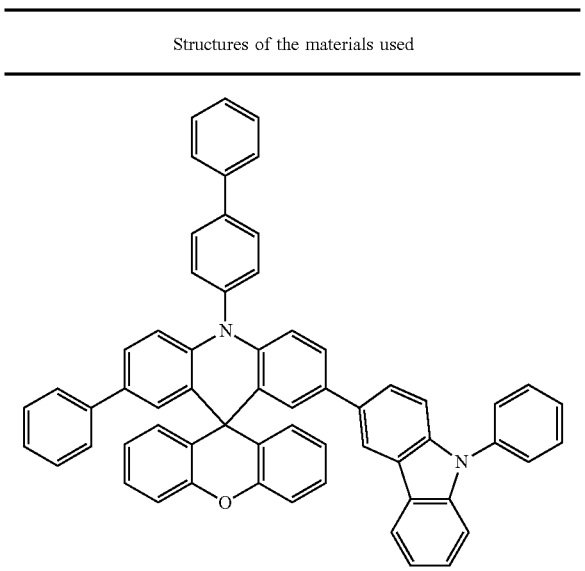
HTM3
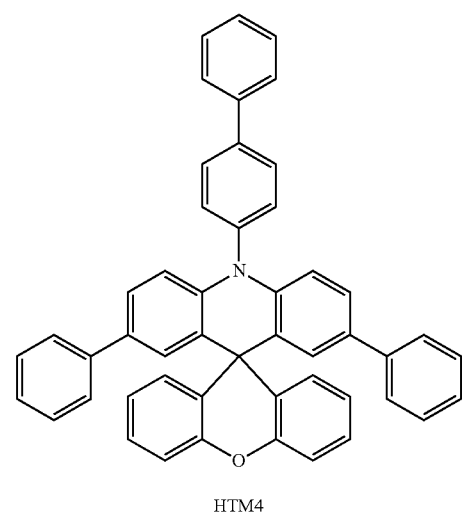
HTM4
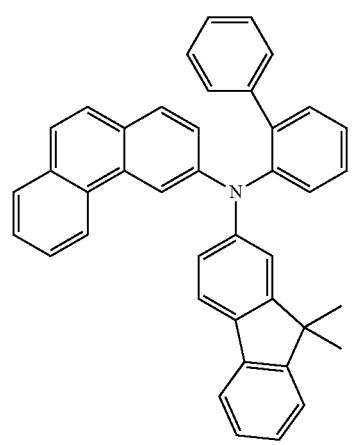 [SMILES: CC1(C)c2ccccc2-c2ccc(N(c3ccc4ccc5ccccc5c4c3)c3ccccc3-c3ccccc3)cc21]
HTM5
TABLE 1-continued
Structures of the materials used
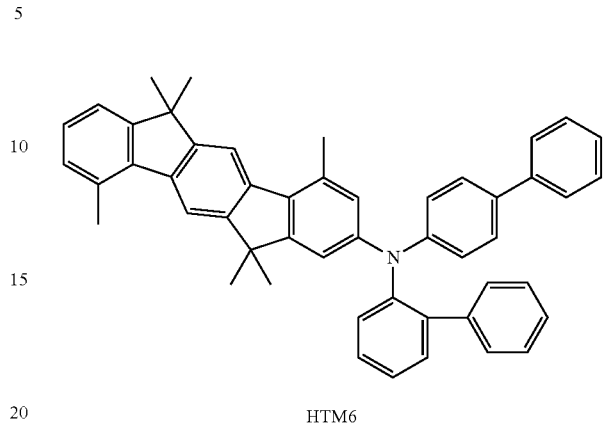
HTM6
HAT-CN

TABLE 2

Structure of the OLEDs

| Ex. | HIL1 Thickness/ nm | HTL Thickness/ nm | HIL2 Thickness/ nm | EBL Thickness/ nm | EML Thickness/ nm | ETL Thickness/ nm | EIL Thickness/ nm |
|---|---|---|---|---|---|---|---|
| V1 | HIM1:F4TCNQ (3%) 20 nm | HIM1 175 nm | | HTM1 20 nm | H1:SEB1 (5%) 20 nm | ETM (50%):LiQ (50%) 30 nm | LiQ 1 nm |
| E1 | HIM1:F4TCNQ (3%) 20 nm | HIM1 155 nm | HTM1:F4TCNQ (3%) 20 nm | HTM1 20 nm | H1:SEB1 (5%) 20 nm | ETM (50%):LiQ (50%) 30 nm | LiQ 1 nm |
| V2 | HIM1:F4TCNQ (3%) 20 nm | HIM1 210 nm | | HTM1 20 nm | H2:TEG (10%) 40 nm | ETM (50%):LiQ (50%) 30 nm | LiQ 1 nm |
| E2 | HIM1:F4TCNQ (3%) 20 nm | HIM1 190 nm | HTM1:F4TCNQ (3%) 20 nm | HTM1 20 nm | H2:TEG (10%) 40 nm | ETM (50%):LiQ (50%) 30 nm | LiQ 1 nm |
| V3 | HIM1:F4TCNQ (3%) 20 nm | HIM1 175 nm | | HTM2 20 nm | H1:SEB1 (5%) 20 nm | ETM (50%):LiQ (50%) 30 nm | LiQ 1 nm |
| E3 | HIM1:F4TCNQ (3%) 20 nm | HIM1 155 nm | HTM2:F4TCNQ (3%) 20 nm | HTM2 20 nm | H1:SEB1 (5%) 20 nm | ETM (50%):LiQ (50%) 30 nm | LiQ 1 nm |
| E4 | HIM1:F4TCNQ (3%) 20 nm | HIM1 155 nm | HTM1:F4TCNQ (3%) 20 nm | HTM2 20 nm | H1:SEB1 (5%) 20 nm | ETM (50%):LiQ (50%) 30 nm | LiQ 1 nm |
| V4 | HIM1:F4TCNQ (3%) 20 nm | HIM1 175 nm | | HTM3 20 nm | H1:SEB1 (5%) 20 nm | ETM (50%):LiQ (50%) 30 nm | LiQ 1 nm |
| E5 | HIM1:F4TCNQ (3%) 20 nm | HIM1 155 nm | HTM3:F4TCNQ (3%) 20 nm | HTM3 20 nm | H1:SEB1 (5%) 20 nm | ETM (50%):LiQ (50%) 30 nm | LiQ 1 nm |
| E6 | HIM1:F4TCNQ (3%) 20 nm | HIM1 155 nm | HTM1:F4TCNQ (3%) 20 nm | HTM3 20 nm | H1:SEB1 (5%) 20 nm | ETM (50%):LiQ (50%) 30 nm | LiQ 1 nm |
| V5 | HIM1:F4TCNQ (3%) 20 nm | HIM1 175 nm | | NPB 20 nm | H1:SEB1 (5%) 20 nm | ETM 30 nm | LiQ 3 nm |
| E7 | HIM1:F4TCNQ (3%) 20 nm | HIM1 155 nm | NPB:F4TCNQ (3%) 20 nm | NPB 20 nm | H1:SEB1 (5%) 20 nm | ETM 30 nm | LiQ 3 nm |
| V6 | HIM2:F4TCNQ (3%) 10 nm | HIM2 140 nm | | HTM1 30 nm | H1:SEB2 (5%) 20 nm | ETM (50%):LiQ (50%) 30 nm | LiQ 1 nm |
| V7 | HIM2:F4TCNQ (3%) 150 nm | | | HTM1 30 nm | H1:SEB2 (5%) 20 nm | ETM (50%):LiQ (50%) 30 nm | LiQ 1 nm |
| E8 | HIM2:F4TCNQ (3%) 10 nm | HIM2 140 nm | HTM1:F4TCNQ (3%) 20 nm | HTM1 10 nm | H1:SEB2 (5%) 20 nm | ETM (50%):LiQ (50%) 30 nm | LiQ 1 nm |
| V8 | HIM1:F4TCNQ (3%) 20 nm | HIM1 160 nm | | HTM4 20 nm | H1:SEB1 (5%) 20 nm | ETM (50%):LiQ (50%) 30 nm | LiQ 1 nm |
| E9 | HIM1:F4TCNQ (3%) 20 nm | HIM1 140 nm | HTM5:F4TCNQ (3%) 20 nm | HTM4 20 nm | H1:SEB1 (5%) 20 nm | ETM (50%):LiQ (50%) 30 nm | LiQ 1 nm |
| V9 | HIM1:F4TCNQ (3%) 20 nm | HIM1 179 nm | | HTM5 20 nm | H1:SEB1 (5%) 20 nm | ETM (50%):LiQ (50%) 30 nm | LiQ 1 nm |
| E10 | HIM1:F4TCNQ (3%) 20 nm | HIM1 155 nm | HTM6:F4TCNQ (3%) 20 nm | HTM5 20 nm | H1:SEB1 (5%) 20 nm | ETM (50%):LiQ (50%) 30 nm | LiQ 1 nm |
| E11 | HIM1:F4TCNQ (3%) 20 nm | HIM1 155 nm | HTM1:F4TCNQ (3%) 20 nm | HTM5 20 nm | H1:SEB1 (5%) 20 nm | ETM (50%):LiQ (50%) 30 nm | LiQ 1 nm |
| V10 | HIM1:F4TCNQ (3%) 20 nm | HIM1 175 nm | | HTM6 20 nm | H1:SEB1 (5%) 20 nm | ETM (50%):LiQ (50%) 30 nm | LiQ 1 nm |
| E12 | HIM1:F4TCNQ (3%) 20 nm | HIM1 155 nm | HTM6:F4TCNQ (3%) 20 nm | HTM6 20 nm | H1:SEB1 (5%) 20 nm | ETM (50%):LiQ (50%) 30 nm | LiQ 1 nm |
| E13 | HIM1:F4TCNQ (3%) 20 nm | HIM1 155 nm | HTM1:F4TCNQ (3%) 20 nm | HTM6 20 nm | H1:SEB1 (5%) 20 nm | ETM (50%):LiQ (50%) 30 nm | LiQ 1 nm |
| V11 | HIM2:F4TCNQ (3%) 10 nm | HIM2 140 nm | Hat-CN 10 nm | HTM1 20 nm | H1:SEB2 (5%) 20 nm | ETM (50%):LiQ (50%) 30 nm | LiQ 1 nm |

Example 1

A reference sample V1 was prepared and compared with sample E1 according to the invention. HIM1 and HTM1 are the same material in this example. Reference sample V1 has a voltage of 4.0 V, an external quantum efficiency of 7.7% and a lifetime (LT80 @ 60 mA/cm$^2$) of 105 h at a current density of 10 mA/cm$^2$. By comparison, both the external quantum efficiency at a current density of 10 mA/cm$^2$ is higher at 8.1% in the case of sample E1 according to the invention, and also the lifetime measured (LT80 @ 60 mA/cm$^2$) of 220 h is shorter at the same time as a lower voltage of 3.9 V. The colour coordinates according to CIE 1931 are (0.14/0.14) for comparative sample V1 and (0.14/0.14) for sample E1 according to the invention.

A further comparison is reference sample V2 with sample E2 according to the invention. Here too, materials HIM1 and HTM1 are identical. Here too, sample E2 according to the invention has both a higher quantum efficiency (@ 2 mA/cm$^2$) of 20.0% compared with reference sample V2 of 19.9% and also a longer lifetime (LT80 @ 20 mA/cm$^2$) of 165 h compared with reference sample E2 of 110 h. The voltage of the reference sample (@ 2 mA) was 3.3 V and was higher than the voltage of sample E2 of 3.1 V. The CIE colour coordinates of the samples were (0.34/0.63).

Example 2

In this example, different materials are present in each of hole-transport layers A and C.

Compared with reference sample V3, samples E3 and E4 according to the invention exhibit a significantly longer lifetime (LT80 @ 60 mA/cm$^2$) of 305 h (E3) and 135 h (E4) compared with 45 h (V3). The quantum efficiency (@ 10 mA/cm$^2$) of reference sample V3 is, at 8.9%, somewhat higher than that of sample E3, at 8.3%, and somewhat lower than that of sample E4, at 9.8%. The voltage of the reference sample of 4.4 V at 10 mA/cm$^2$ was higher than that of samples E3, at 4.1 V, and E4, at 4.2 V.

Example 3

In this example, different materials are present in each of hole-transport layers A and C.

Compared with samples E5 and E6 according to the invention, reference sample V4 exhibits a significantly shorter lifetime (LT80 @ 60 mA/cm$^2$) of 75 h compared with 175 h for E5 and 145 h for E6. The voltage of the two samples according to the invention is in each case lower at 4.0 V (E5) and 3.8 V (E6) compared with the reference of 4.2 V at 10 mA/cm$^2$.

Example 4

In this example, different materials are present in hole-transport layers A and C.

Compared with sample E7 according to the invention, reference sample V5 exhibits a shorter lifetime (LT80 @ 60 mA/cm$^2$) of 105 h compared with E7 of 125 h and a higher voltage of 3.8 V compared with 3.6 V at 10 mA/cm$^2$.

Example 5

In this example, different materials are present in hole-transport layers A and C.

Compared with sample E8 according to the invention, reference samples V6 and V7 exhibit a shorter lifetime (LT80 @ 80 mA/cm$^2$) of 65 h (V6) or 95 h (V7) compared with 270 h for E8 and higher voltages of 4.6 V (V6) and 4.1 V (V7) compared with 4.0 V for E8 at 10 mA/cm$^2$. The CIE colour coordinates for all three samples were at (0.14/0.19).

By comparison, although the reference sample V11, which has a layer comprising compound HAT-CN instead of the p-doped interlayer, also has very low voltages of 3.8 V, it has, however, a shorter lifetime (LT80 @ 80 mA/cm$^2$) of about 210 h.

Example 6

In this example, different materials are present in hole-transport layers A and C.

Compared with reference sample V8, sample E9 according to the invention exhibits a better lifetime (LT80 @ 60 mA/cm$^2$) of 215 h compared with 155 h and lower voltages of 3.7 V compared with 4.4 V.

Example 7

In this example, different materials are present in hole-transport layers A and C.

Compared with samples E10 and E11 according to the invention, reference sample V9 exhibits a shorter lifetime (LT80 @ 60 mA/cm$^2$) of 175 h and a lower efficiency (EQE @ 10 mA) of 9.2% compared with 210 h and 9.7% for E10 and 255 h and 9.8% EQE for E11. Here too, the voltage of the reference sample is, at 4.0 V, higher than that of E10, at 3.7 V, and E11, at 3.8 V, at 10 mA/cm$^2$.

Example 8

In this example, different materials are present in hole-transport layers A and C.

Compared with samples E12 and E13 according to the invention, reference sample V10 exhibits a shorter lifetime (LT80 @ 60 mA/cm$^2$) of 165 h compared with 450 h (E12) and 405 h (E13). Here too, the voltage of the reference sample is, at 4.3 V, higher than that of E12, at 3.96 V, and E13, at 3.7 V, at 10 mA/cm$^2$.

As shown in the above examples, the devices according to the invention have higher efficiency and preferably a longer lifetime than devices in accordance with the prior art. Furthermore, the operating voltage of the devices is preferably lower than in the case of devices in accordance with the prior art.

The invention claimed is:

1. An electronic device comprising anode, cathode and at least one emitting layer arranged between the anode and the cathode, and at least one hole-transport layer A, comprising at least one hole-transport material which is selected from tri-arylamine compounds, at least one p-doped hole-transport layer B, comprising at least one p-dopant and at least one hole-transport material matrix which is selected from triarylamine compounds, at least one hole-transport layer C, comprising at least one hole-transport material, which is selected from tri-arylamine compounds, where hole-transport layers A, B and C are arranged between the anode and the emitting layer, and where hole-transport layer B is arranged on the cathode side of hole-transport layer A, and hole-transport layer C is arranged on the cathode side of hole-transport layer B and wherein hole-transport layers A, B and C and are directly adjacent to one another and the hole-transport layers A, B and C each comprise one or more identical or different monotriarylamine compounds.

2. The electronic device according to claim 1, wherein the device is selected from organic light-emitting transistors (OLETs), organic light-emitting electrochemical cells (OLECs), organic laser diodes (O-lasers) or organic electroluminescent devices (OLEDs).

3. The electronic device according to claim 1, wherein the anode comprises tungsten oxide, molybdenum oxide and/or vanadium oxide, and/or in that a p-doped hole-transport layer A', comprising at least one p-dopant and a hole-transport material matrix, is arranged between the anode and hole-transport layer A.

4. The electronic device according to claim 3, wherein hole-transport layers A, B, C and A' each comprise one or more identical or different monotriarylamine compounds.

5. The electronic device according to claim 3, wherein at least one of hole-transport layers A, B, C and A' comprises at least one compound of one of the formulae (I) to (VI)

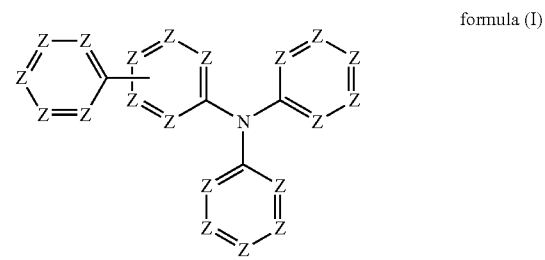

formula (I)

-continued

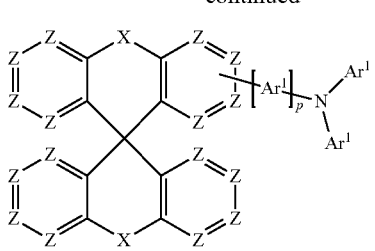
formula (II)

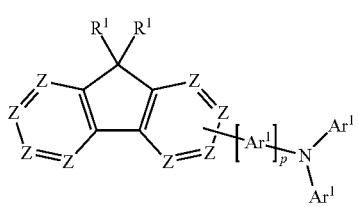
formula (III)

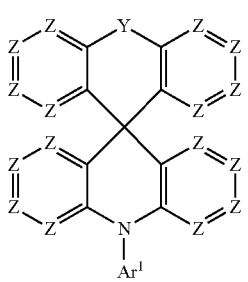
formula (IV)

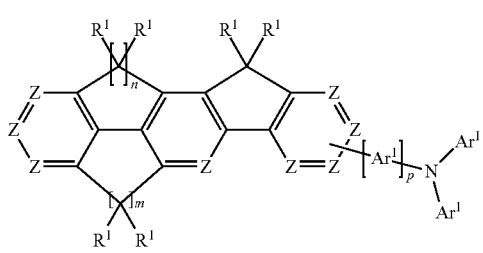
formula (V)

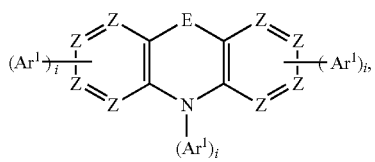
formula (VI)

where:
- Z is on each occurrence, identically or differently, N or $CR^1$, where Z is equal to C if a substituent is bonded;
- X, Y are on each occurrence, identically or differently, a single bond, O, S, Se, $BR^1$, $C(R^1)_2$, $Si(R^1)_2$, $NR^1$, $PR^1$, $C(R^1)_2$—$C(R^1)_2$ or $CR^1$=$CR^1$;
- E is O, S, Se, $BR^1$, $C(R^1)_2$, $Si(R^1)_2$, $NR^1$, $PR^1$, $C(R^1)_2$—$C(R^1)_2$ or $CR^1$=$CR^1$;
- $Ar^1$ is on each occurrence, identically or differently, an aromatic or heteroaromatic ring system having 5 to 60 aromatic ring atoms, which may be substituted by one or more radicals $R^1$; and
- $R^1$ is on each occurrence, identically or differently, H, D, F, Cl, Br, I, CHO, C(=O)$R^2$, P(=O)$(R^2)_2$, S(=O)$R^2$, S(=O)$_2R^2$, $CR^2$=$CR^2R^2$, CN, $NO_2$, Si$(R^2)_3$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^2$, where one or more non-adjacent $CH_2$ groups may be replaced by $R^2C$=$CR^2$, Si$(R^2)_2$, Ge$(R^2)_2$, Sn$(R^2)_2$, C=O, C=S, C=Se, C=$NR^2$, P(=O)$(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or a combination of these systems; two or more adjacent substituents $R^1$ here may also form a mono- or polycyclic, aliphatic or aromatic ring system with one another;

- $R^2$ is on each occurrence, identically or differently, H, D, CN or an aliphatic, aromatic and/or heteroaromatic hydrocarbon radical having 1 to 20 C atoms, in which, in addition, H atoms may be replaced by D or F; two or more adjacent substituents $R^2$ here may also form a mono- or polycyclic, aliphatic or aromatic ring system with one another;

- i is on each occurrence, identically or differently, 0 or 1, where the sum of all i is at least equal to 1;
- p is equal to 0 or 1;
- m, n are, identically or differently, 0 or 1, where the sum of m and n is equal to 1 or 2.

6. The electronic device according to claim 3, wherein each one of hole-transport layers A, B, C and A' comprises at least one compound of one of the formulae (I) to (VI)

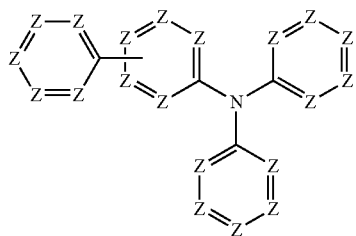
formula (I)

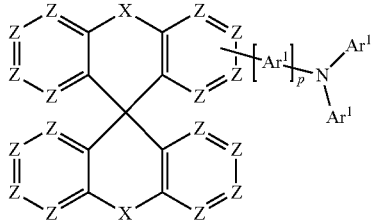
formula (II)

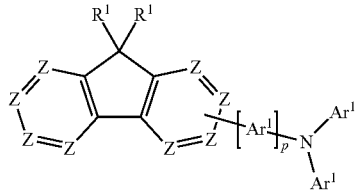
formula (III)

-continued formula (IV)

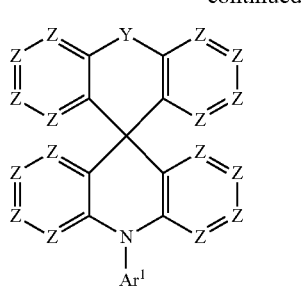

formula (V)

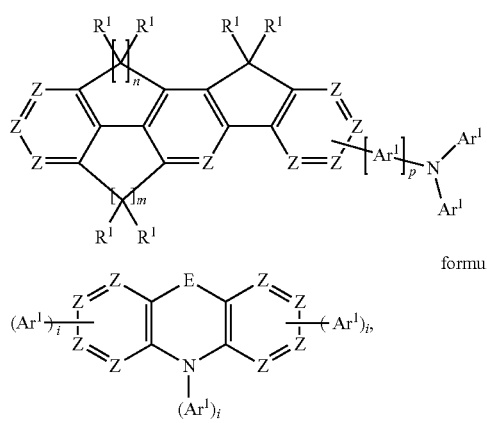

formula (VI)

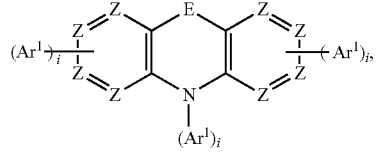

where:
- Z is on each occurrence, identically or differently, N or CR¹, where Z is equal to C if a substituent is bonded;
- X, Y are on each occurrence, identically or differently, a single bond, O, S, Se, BR¹, C(R¹)₂, Si(R¹)₂, NR¹, PR¹, C(R¹)₂-C(R¹)₂ or CR¹=CR¹;
- E is O, S, Se, BR¹, C(R¹)₂, Si(R¹)₂, NR¹, PR¹, C(R¹)₂-C(R¹)₂ or CR¹=CR¹;
- Ar₁ is on each occurrence, identically or differently, an aromatic or heteroaromatic ring system having 5 to 60 aromatic ring atoms, which may be substituted by one or more radicals R¹; and
- R¹ is on each occurrence, identically or differently, H, D, F, Cl, Br, I, CHO, C(=O)R², P(=O)(R²)₂, S(=O)R², S(=O)₂R², CR²=CR²R², CN, NO₂, Si(R²)₃, OSO₂R², a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R², where one or more non-adjacent CH₂ groups may be replaced by R²C=CR², C≡C, Si(R²)₂, Ge(R²)₂, Sn(R²)₂, C=O, C=S, C=Se, C=NR², P(=O)(R²), SO, SO₂, NR², O, S or CONR² and where one or more H atoms may be replaced by D, F, Cl, Br, I, CN or NO₂, or an aromatic or heteroaromatic ring system having 5 to 60 aromatic ring atoms, which may in each case be substituted by one or more radicals R², or a combination of these systems; two or more adjacent substituents R¹ here may also form a mono- or polycyclic, aliphatic or aromatic ring system with one another;
- R² is on each occurrence, identically or differently, H, D, CN or an aliphatic, aromatic and/or heteroaromatic hydrocarbon radical having 1 to 20 C atoms, in which, in addition, H atoms may be replaced by D or F; two or more adjacent substituents R² here may also form a mono- or polycyclic, aliphatic or aromatic ring system with one another;
- i is on each occurrence, identically or differently, 0 or 1, where the sum of all i is at least equal to 1;
- p is equal to 0 or 1;
- m, n are, identically or differently, 0 or 1, where the sum of m and n is equal to 1 or 2.

7. The electronic device according to claim 3, wherein at least one of hole-transport layers A, B, C and A' comprises at least one compound of one of the formula (II) or (III)

formula (II)

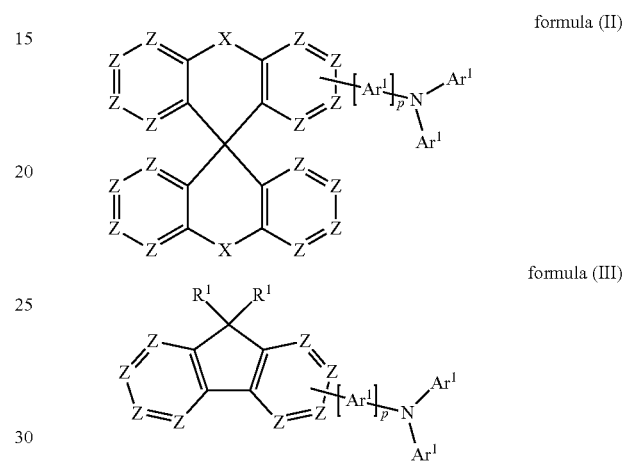

formula (III)

where:
- Z is on each occurrence, identically or differently, N or CR¹, where Z is equal to C if a substituent is bonded;
- X is a single bond;
- Ar¹ is on each occurrence, identically or differently, an aromatic ring system having 5 to 60 aromatic ring atoms, which may be substituted by one or more radicals R¹; and
- R¹ is on each occurrence, identically or differently, H, D, F, Cl, Br, I, CHO, C(=O)R², P(=O)(R²)₂, S(=O)R², S(=O)₂R², CR²=CR²R², CN, NO₂, Si(R²)₃, OSO₂R², a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R², where one or more non-adjacent CH₂ groups may be replaced by R²C=CR², C≡C, Si(R²)₂, Ge(R²)₂, Sn(R²)₂, C=O, C=S, C=Se, C=NR², P(=O)(R²), SO, SO₂, NR², O, S or CONR² and where one or more H atoms may be replaced by D, F, Cl, Br, I, CN or NO₂, or an aromatic ring system having 5 to 60 aromatic ring atoms, which may in each case be substituted by one or more radicals R²;
- R² is on each occurrence, identically or differently, H, D, CN or an aliphatic, aromatic hydrocarbon radical having 1 to 20 C atoms, in which, in addition, H atoms may be replaced by D or F; and
- p is equal to 0 or 1.

8. The electronic device according to claim 7, wherein each one of hole-transport layers A, B, C and A' comprises at least one compound of one of the formula (II) or (III).

9. The electronic device according to claim 8, wherein hole-transport layer A comprises no p-dopant.

10. The electronic device according to claim 1, wherein hole-transport layer A has a thickness of 100 to 300 nm.

11. The electronic device according to claim 1, wherein hole-transport layer A comprises no p-dopant.

12. The electronic device according to claim 1, wherein the p-dopant is selected from quinodimethane compounds, azaindenofluorenediones, azaphenalenes, azatriphenylenes, $I_2$, metal halides, metal oxides, transition-metal complexes and transition-metal oxides.

13. The electronic device according to claim 1, wherein the p-dopant is present in hole-transport layer B in a concentration of 0.1 to 20% by vol.

14. The electronic device according to claim 1, wherein hole-transport layer C comprises no p-dopant.

15. The electronic device according to claim 1, wherein hole-transport layer B comprises the same compound as hole-transport material matrix as hole-transport layer C does as hole-transport material.

16. A light source in a lighting application which comprises the electronic device according to claim 1.

17. A light source for use in a medical application which comprises the electronic device according to claim 1.

18. A light source in cosmetic application which comprises the electronic device according to claim 1.

19. The electronic device according to claim 1, wherein each one of hole-transport layers A, B, C and A' comprises at least one compound of one of the formulae (I) to (VI)

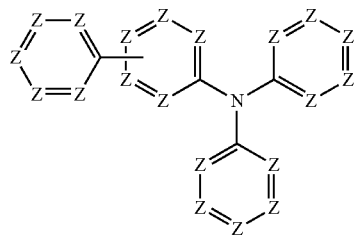

formula (I)

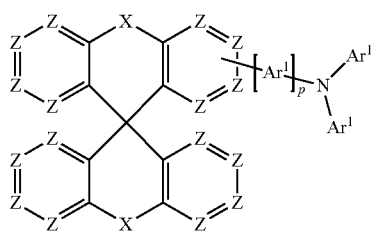

formula (II)

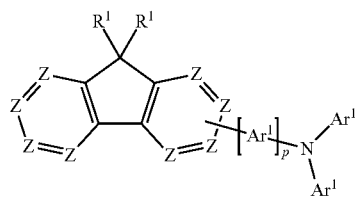

formula (III)

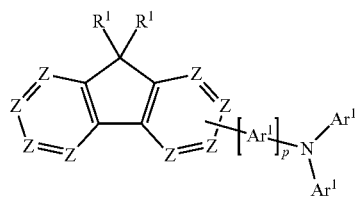

formula (IV)

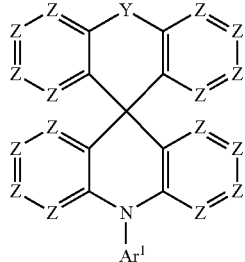

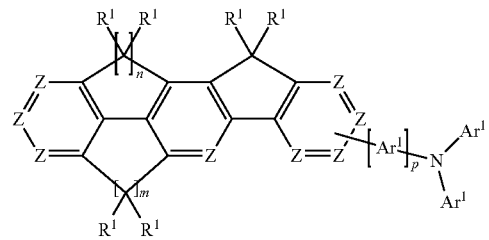

formula (V)

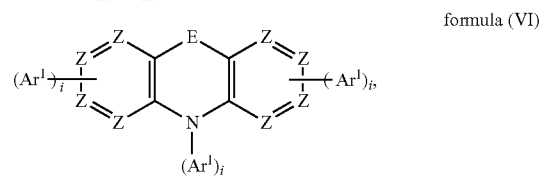

formula (VI)

where:
- Z is on each occurrence, identically or differently, N or $CR^1$, where Z is equal to C if a substituent is bonded;
- X, Y are on each occurrence, identically or differently, a single bond, O, S, Se, $BR^1$, $C(R^1)_2$, $Si(R^1)_2$, $NR^1$, $PR^1$, $C(R^1)_2$-$C(R^1)_2$ or $CR^1=CR^1$;
- E is O, S, Se, $BR^1$, $C(R^1)_2$, $Si(R^1)_2$, $NR^1$, $PR^1$, $C(R^1)_2$-$C(R^1)_2$ or $CR^1=CR^1$;
- $Ar^1$ is on each occurrence, identically or differently, an aromatic or heteroaromatic ring system having 5 to 60 aromatic ring atoms, which may be substituted by one or more radicals $R^1$; and
- $R^1$ is on each occurrence, identically or differently, H, D, F, Cl, Br, I, CHO, $C(=O)R^2$, $P(=O)(R^2)_2$, $S(=O)R^2$, $S(=O)_2R^2$, $CR^2=CR^2R^2$, CN, $NO_2$, $Si(R^2)_3$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals $R^2$, where one or more non-adjacent $CH_2$ groups may be replaced by $R^2C=CR^2$, $C\equiv C$, $Si(R^2)_2$, $Ge(R^2)_2$, $Sn(R^2)_2$, C=O, C=S, C=Se, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or a combination of these systems; two or more adjacent substituents $R^1$ here may also form a mono- or polycyclic, aliphatic or aromatic ring system with one another;
- $R^2$ is on each occurrence, identically or differently, H, D, CN or an aliphatic, aromatic and/or heteroaromatic hydrocarbon radical having 1 to 20 C atoms, in which, in addition, H atoms may be replaced by D or F; two or more adjacent substituents $R^2$ here may also form a mono- or polycyclic, aliphatic or aromatic ring system with one another;
- i is on each occurrence, identically or differently, 0 or 1, where the sum of all i is at least equal to 1;
- p is equal to 0 or 1;
- m, n are, identically or differently, 0 or 1, where the sum of m and n is equal to 1 or 2.

20. The electronic device according to claim 16, wherein at least one of hole-transport layers A, B, C and A' comprises at least one compound of one of the formula (II) or (III)

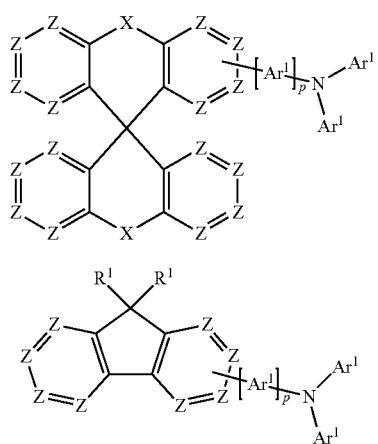

formula (II)

formula (III)

where:
- Z is on each occurrence, identically or differently, N or CR$^1$, where Z is equal to C if a substituent is bonded;
- X is a single bond;
- Ar$^1$ is on each occurrence, identically or differently, an aromatic ring system having 5 to 60 aromatic ring atoms, which may be substituted by one or more radicals R$^1$; and
- R$^1$ is on each occurrence, identically or differently, H, D, F, Cl, Br, I, CHO, C(=O)R$^2$, P(=O)(R$^2$)$_2$, S(=O)R$^2$, S(=O)$_2$R$^2$, CR$^2$=CR$^2$R$^2$, CN, NO$_2$, Si(R$^2$)$_3$, OSO$_2$R$^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R$^2$, where one or more non-adjacent CH$_2$ groups may be replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more H atoms may be replaced by D, F, Cl, Br, I, CN or NO$_2$, or an aromatic ring system having 5 to 60 aromatic ring atoms, which may in each case be substituted by one or more radicals R$^2$;
- R$^2$ is on each occurrence, identically or differently, H, D, CN or an aliphatic, aromatic hydrocarbon radical having 1 to 20 C atoms, in which, in addition, H atoms may be replaced by D or F; and
- p is equal to 0 or 1.

21. The electronic device according to claim 20, wherein each one of hole-transport layers A, B, C and A' comprises at least one compound of one of the formula (II) or (III).

22. The electronic device according to claim 21, wherein hole-transport layer A comprises no p-dopant.

23. An electronic device comprising anode, cathode and at least one emitting layer arranged between the anode and the cathode, and
- at least one hole-transport layer A, comprising at least one hole-transport material which is selected from tri-arylamine compounds,
- at least one p-doped hole-transport layer B, comprising at least one p-dopant and at least one hole-transport material matrix which is selected from triarylamine compounds,
- at least one hole-transport layer C, comprising at least one hole-transport material, which is selected from tri-arylamine compounds, where hole-transport layers A, B and C are arranged between the anode and the emitting layer, and
where hole-transport layer B is arranged on the cathode side of hole-transport layer A, and hole-transport layer C is arranged on the cathode side of hole-transport layer B and wherein hole-transport layers A, B and C and are directly adjacent to one another and
wherein the hole-transport layer A comprises the same compound as hole-transport material as hole-transport layer A' does as hole-transport material matrix.

24. An electronic device comprising anode, cathode and at least one emitting layer arranged between the anode and the cathode, and
- at least one hole-transport layer A, comprising at least one hole-transport material which is selected from tri-arylamine compounds,
- at least one p-doped hole-transport layer B, comprising at least one p-dopant and at least one hole-transport material matrix which is selected from triarylamine compounds,
- at least one hole-transport layer C, comprising at least one hole-transport material, which is selected from tri-arylamine compounds, where hole-transport layers A, B and C are arranged between the anode and the emitting layer, and
where hole-transport layer B is arranged on the cathode side of hole-transport layer A, and hole-transport layer C is arranged on the cathode side of hole-transport layer B and wherein hole-transport layers A, B and C and are directly adjacent to one another and wherein the hole-transport materials of hole-transport layers A and C are different.

* * * * *